US010839712B2

(12) United States Patent
Carr et al.

(10) Patent No.: US 10,839,712 B2
(45) Date of Patent: Nov. 17, 2020

(54) MONITORING LEARNING PERFORMANCE USING NEUROFEEDBACK

(71) Applicant: International Business Machines Corporation, Armonk, NY (US)

(72) Inventors: Kevin Gerard Carr, Wappingers Falls, NY (US); Payel Das, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 419 days.

(21) Appl. No.: 15/260,511

(22) Filed: Sep. 9, 2016

(65) Prior Publication Data

US 2018/0075772 A1   Mar. 15, 2018

(51) Int. Cl.
*G09B 19/00* (2006.01)
*G09B 19/06* (2006.01)
(Continued)

(52) U.S. Cl.
CPC ............ *G09B 19/00* (2013.01); *A61B 5/0075* (2013.01); *A61B 5/0482* (2013.01);
(Continued)

(58) Field of Classification Search
CPC ........... G09B 19/00; G09B 5/00; G09B 23/28
See application file for complete search history.

(56) References Cited

U.S. PATENT DOCUMENTS 4,203,452 A    5/1980  Cohen
5,447,166 A *  9/1995  Gevins ................ A61B 5/0484
                                              128/925
(Continued)

FOREIGN PATENT DOCUMENTS

CN    202486999 U    10/2012
CN    103815902 A     5/2014

OTHER PUBLICATIONS

Carr, et al., "Method for Monitoring Student Learning and Behavior in a Classroom Setting," Last Accessed: Sep. 6, 2016, 9 pages.
(Continued)

*Primary Examiner* — James B Hull
(74) *Attorney, Agent, or Firm* — Amin, Turocy & Watson, LLP

(57) ABSTRACT

Techniques that facilitate monitoring learning performance using neurofeedback are described. In one embodiment, a system is provided that comprises a memory that stores computer-executable components and a processor that executes computer-executable components stored in the memory. In one implementation, the computer-executable components comprise a feedback component that receives first feedback information regarding mental function of a user in association with participation in a learning experience, wherein the first feedback information is captured via a NIRS spectroscopy sensor worn by the user. The computer-executable components further comprise an assessment component that determines learning performance information for the user based on the first feedback information, wherein the learning performance information reflects the user's learning of content presented to the user in the learning experience, and a notification component that generates a notification based on the learning performance information indicating the user's learning of the content is below a defined learning performance level.

20 Claims, 10 Drawing Sheets

(51) Int. Cl.
*A61B 5/0482* (2006.01)
*A61B 5/00* (2006.01)
*G09B 5/08* (2006.01)
*G09B 7/02* (2006.01)
*A61B 5/02* (2006.01)
*A61B 5/1455* (2006.01)
*A61B 5/16* (2006.01)

(52) U.S. Cl.
CPC .............. *A61B 5/4064* (2013.01); *G09B 5/08* (2013.01); *G09B 7/02* (2013.01); *G09B 19/06* (2013.01); *A61B 5/02028* (2013.01); *A61B 5/14551* (2013.01); *A61B 5/168* (2013.01); *A61B 5/7264* (2013.01)

(56) References Cited

U.S. PATENT DOCUMENTS

| | | | |
|---|---|---|---|
| 5,740,812 A | 4/1998 | Cowan | |
| 5,884,626 A | 3/1999 | Kuroda et al. | |
| 6,097,981 A * | 8/2000 | Freer | G09B 19/00 600/544 |
| 6,155,974 A * | 12/2000 | Fish | A61B 5/0006 128/903 |
| 6,163,281 A * | 12/2000 | Torch | A61B 3/0066 340/575 |
| 6,402,520 B1 * | 6/2002 | Freer | A61B 5/0482 434/236 |
| 6,542,081 B2 * | 4/2003 | Torch | A61B 3/0066 340/573.1 |
| 7,020,508 B2 * | 3/2006 | Stivoric | A61B 5/0205 |
| RE39,539 E * | 4/2007 | Torch | A61B 3/0066 340/573.1 |
| 7,285,090 B2 * | 10/2007 | Stivoric | A61B 5/01 600/300 |
| 8,296,172 B2 * | 10/2012 | Marci | G06Q 10/10 705/7.29 |
| 8,398,546 B2 * | 3/2013 | Pacione | A61B 5/411 128/920 |
| 9,101,279 B2 * | 8/2015 | Ritchey | G16H 40/63 |
| 9,111,460 B2 | 8/2015 | Whyte | |
| 9,224,309 B2 | 12/2015 | Mutlu et al. | |
| 9,405,366 B2 * | 8/2016 | Segal | G06F 3/015 |
| 9,579,060 B1 * | 2/2017 | Lisy | A61B 5/6803 |
| 9,711,056 B1 * | 7/2017 | Nguyen | A61B 5/165 |
| 9,936,916 B2 * | 4/2018 | Sahin | A61B 5/16 |
| 9,994,228 B2 * | 6/2018 | Krueger | A61M 21/00 |
| 10,071,245 B1 * | 9/2018 | Phillips | A61N 1/36025 |
| 2015/0379400 A1 * | 12/2015 | Tatourian | H04L 67/22 706/46 |
| 2017/0231501 A1 * | 8/2017 | Culver | A61B 5/7207 600/425 |
| 2018/0085000 A1 * | 3/2018 | Weffers-Albu | A61B 5/7246 |

OTHER PUBLICATIONS

List of IBM Patents or Applications Treated as Related.
Ogawa, et al., "Relationship between working memory performance and neural activation measured using near-infrared spectroscopy," Brain Behav. Jul. 2014; 4(4): 544-551.

* cited by examiner

MONITORING LEARNING PERFORMANCE USING NEUROFEEDBACK

BACKGROUND

The subject disclosure relates to monitoring learning performance using neurofeedback.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments, systems, computer-implemented methods, apparatus and/or computer program products that facilitate monitoring learning performance using neurofeedback are described.

According to an embodiment, a system is provided that can comprise a memory that stores computer-executable components and a processor that executes computer-executable components stored in the memory. In one or more implementations, the computer-executable components comprise a feedback component that receives first feedback information regarding mental function of a user in association with participation in a learning experience, wherein the first feedback information is captured via a near-infrared spectroscopy (NIRS) spectroscopy sensor worn by the user. The computer-executable components further comprise an assessment component that determines learning performance information for the user based on the first feedback information, wherein the learning performance information reflects user learning of the content presented to the user in the learning experience, and a notification component that generates a notification based on the learning performance information indicating the user's learning of content is below a defined learning performance level. In various implementations, the first feedback information comprises haemodynamic information selected from a group consisting of working memory performance levels, stress levels and attention levels of the user.

In one or more implementations, the feedback component further receives second feedback information regarding the mental function of the user in association with the participation in the learning experience, wherein the second feedback information is captured via an electroencephalogram (EEG) sensor worn by the user, and wherein the assessment component further determines the learning performance information for the user based on the first feedback information and the second feedback information. For example, the learning performance information can comprise performance levels of the user with respect to defined cognitive function areas associated with the mental function of the user. With these implementations, the defined cognitive function areas can be selected from a group consisting of: attention, familiarity, mental effort, working memory, linguistic acquisition, social learning, and mediation.

In another embodiment, a computer-implemented method is provided. In one example, the computer-implemented method comprises receiving, by a device operatively coupled to a processor, first feedback information regarding mental activity of a user in a learning environment, wherein the first feedback information is captured via a NIRS spectroscopy sensor worn by the user. The computer-implemented method can further comprise determining, by the device, learning performance information for the user based on the first feedback information, wherein the learning performance information comprises learning performance levels of the user with respect to defined cognitive function areas associated with the mental activity of the user, and generating, by the device, a notification based on the learning performance information indicating the user's learning performance is below a defined learning performance level. For example, the defined cognitive function areas can be selected from a group consisting of: attention, familiarity, mental effort, working memory, linguistic acquisition, social learning, and mediation. In one or more implementations, the computer-implemented method can further comprise receiving, by the device, second feedback information regarding the mental activity of the user in the learning environment, wherein the second feedback information is captured via an EEG sensor worn by the user, and wherein the determining the learning performance information comprises determining the learning performance information for the user based on the first feedback information and the second feedback information.

In another embodiment, a computer program product for monitoring learning performance based on neurofeedback, the computer program product comprising a computer readable storage medium having program instructions embodied therewith. The program instructions executable by a processing component to cause the processing component to receive neurofeedback information regarding mental function of a user in a learning context, wherein the neurofeedback information is captured via a near-infrared spectroscopy sensor worn by the user, and determine learning performance information for the user based on the neurofeedback information, wherein the learning performance information reflects the user's learning of content presented to the user in the learning context. The program instructions can further cause the processing component to generate a notification based on the learning performance information indicating the user learning of the content is below a defined learning performance level, and send the notification to a device associated with an entity responsible for teaching the content to the user to facilitate improving the user's learning of the content.

DETAILED DESCRIPTION

Figure 1:
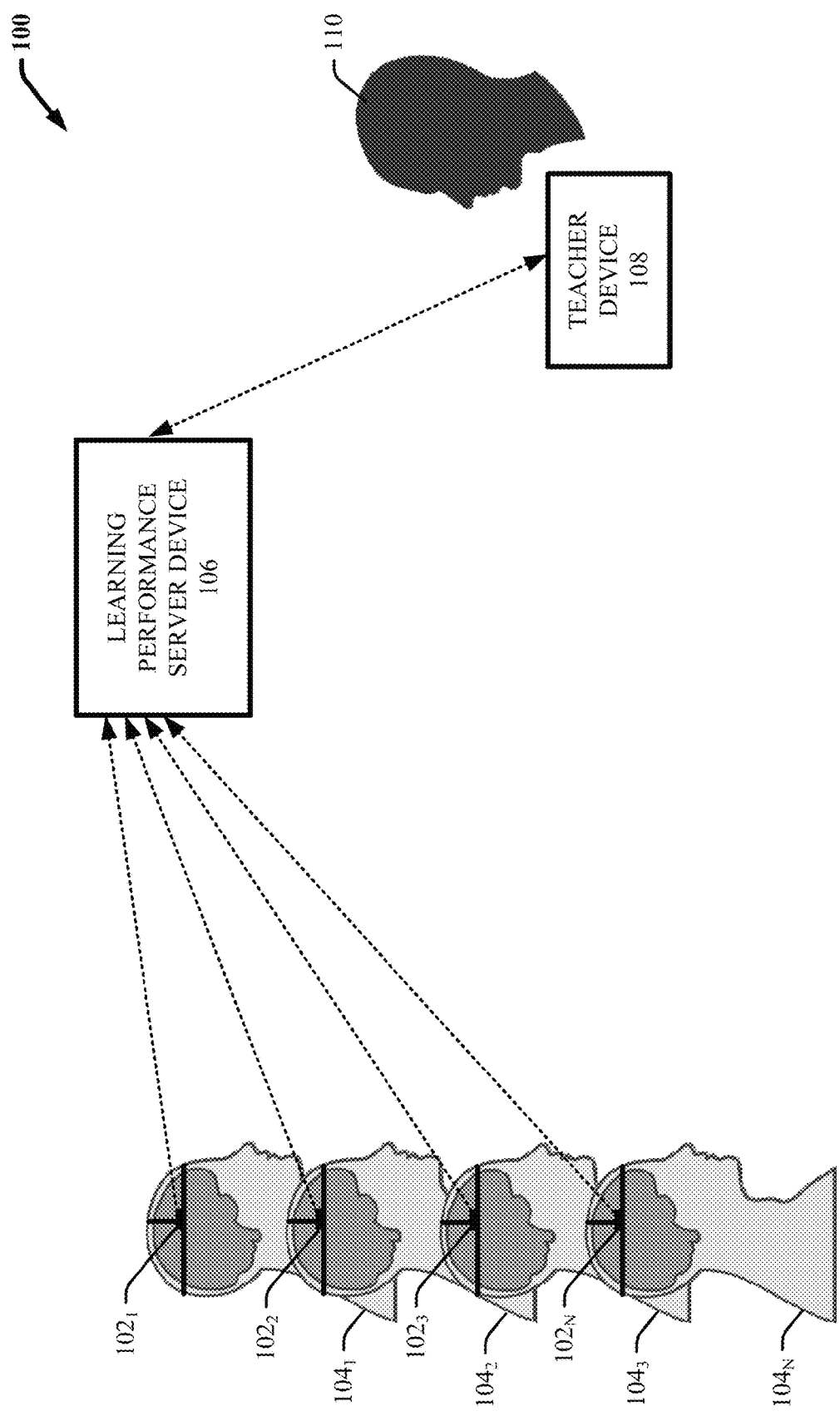
FIG. 1 illustrates an example, non-limiting system that facilitates monitoring learning performance using neurofeedback in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

The subject disclosure is directed to computer processing systems, computer-implemented methods, apparatus and/or computer program products that facilitate monitoring learning performance using neurofeedback. With classroom sizes growing and curriculums becoming more robust and virtually taught, the ability for teachers to find and help struggling students in a timely and effective manner is becoming more and more difficult. Traditionally, teachers use after-task assessments such as quizzes and exams to determine a student's understanding of the material. Accordingly, a student that demonstrates poor learning performance in a particular subject area is generally identified after the subject has been covered and the class has moved on to a new subject. With today's curriculum, there generally is little or no time to address the learning needs of a struggling student once the student is identified after the material has been covered.

The subject disclosure provides techniques for automatically identifying students exhibiting poor learning performance with respect to material that is currently being presented to the students based on minimally invasive multimodal neuroimaging measurements captured from the students as the material is being presented. In particular, in various embodiments, each individual student or learner can wear a device that captures neurofeedback (e.g., neuroimaging measurements) related to the mental activity or mental process of the student while the student is participating in a learning experience, environment or context (e.g., a class, a lecture, a laboratory procedure, a self-study period, an exam, etc.). For example, in various embodiments, the neurofeedback can include neuroimaging measurements that indicate mental performance levels with respect to various defined cognitive function areas including, but not limited to, attention, familiarity, mental effort, working memory, linguistic acquisition, social learning, and/or mediation. In one or more implementations, the device can include a headset or other suitable device that is worn on or near the head of the student (e.g., a headband, an earpiece, an eyepiece, etc.) and comprises one or more neuroimaging sensors that capture the neurofeedback. The neurofeedback for each student (or, in some embodiments, one or more students) can be sent or streamed to another device as it is captured, such as a server device, for processing in real-time or substantially real-time to determine one or more characteristics of the student cognitive processing throughout the learning experience. As used herein, the term "real-time" can mean processing and capturing to data within a defined number of minutes or seconds (e.g., within 10 seconds, within 30 seconds, within 60 seconds, within 2 minutes) after the data is generated. For example, the server device can determine, based on neurofeedback measurements regarding student attention, familiarity, mental effort, working memory, linguistic acquisition, social learning, and/or mediation, a general learning performance score representative of the student's general learning performance for the learning experience. In another example, the server device can determine learning performance scores for the student at different points or periods in time throughout the learning experience. In another example, the server device can determine scores respectively representative of the student learning performance with respect to different defined cognitive state function areas (e.g., attention, familiarity, mental effort, working memory, linguistic acquisition, social learning, mediation, etc.) at different points or periods in time throughout the learning experience and/or for the learning experience as a whole.

Such processing of a student brain activity can facilitate automatically identifying a student who is struggling with the current material and allow for quicker intervention to prevent the student from falling behind. For example, in some embodiments, the teacher, the student, or another suitable entity can be notified in response to a determination that the student is exhibiting low learning performance. In one implementation, a threshold based method can be used to decide when to send an alert to the teacher regarding low learning performance of a student during a lecture or other learning experience orchestrated by the teacher. According to this implementation, the server device can generate and send a notification to the teacher (e.g., at a device employed by the teacher) identifying a student exhibiting low learning performance based on the student learning performance score being below a threshold learning performance score. In one embodiment, notifications generated for students can be collected in a queue and the teacher can request and receive the notifications on demand (e.g., at a time when the teacher is ready to evaluate how the students are performing during class). In some embodiments, the notifications can include information identifying specific cognitive function areas in which a student is exhibiting low learning performance so that the teacher can intervene appropriately.

In some implementations, the server device can generate a learning assessment report that evaluates the learning performance of students for one or more learning experiences. Accordingly, the teacher, the student, or another suitable entity can regularly assess the student learning performance over time to determine how and when the student is struggling and whether the student learning performance is improving. In addition, the teacher can compare the learning performances of students relative to one another to determine collectively what material the students find particularly difficult, interesting, easy, etc., and adjust their curriculum or teaching techniques accordingly. For example, the teacher can go back and look at the collective learning performance feedback for a class as a whole to learn how the students react to specific tasks (e.g., lecture, individual work, small group work, exams, etc.) and adjust the teacher lesson plan accordingly to try and make the time with the students more effective.

In some embodiments, in order to further facilitate evaluating student learning performance, a video and/or audio recording can be captured during the learning experience and correlated to the learning performance feedback received for the respective students. According to these embodiments, student feedback indicative of poor learning performance can be manually (e.g., by the teacher reviewing the video and/or audio recording in conjunction with the student feedback) or automatically correlated to the particular content being discussed at the time the student feedback was generated to identify the particular content the student found difficult, confusing, not engaging, etc. In some embodiments in which video of a student face and/or body language is captured, additional information regarding the student mental state throughout a learning experience can further be discerned using analysis of facial expressions and body language of the student. This additional information can be combined with the neurofeedback to further evaluate the learning performance of the student.

In various exemplary embodiments, the neurofeedback includes neuroimaging measurements captured via one or more NIRS sensors included on or within the device worn by the student (e.g., on or near the student's head). For example, the device can include one or more NIRS sensors that capture quantitative haemodynamic and metabolic information from one or more areas of the brain. The haemodynamic and metabolic information can be correlated to mental performance with respect to one or more defined cognitive function areas, including, but not limited to, working memory performance, mental effort and/or attention. In some embodiments, in addition to neurofeedback captured via one or more NIRS sensors, the neurofeedback can also include neuroimaging measurements captured via one or more electroencephalogram (EEG) sensors included on or within the device worn by the student. For example, EEG measurements can include voltage fluctuations in the time and/or frequency domain that can be correlated to mental performance with respect to various defined cognitive function areas, including but not limited to: attention, familiarity, mental effort, working memory, linguistic acquisition, social learning, and mediation.

Although the terms "student" and "teacher" are used throughout the subject disclosure to refer to the entity whose learning performance is being evaluated and the entity that provides or conducts the learning experience, it should be appreciated that the various techniques for monitoring learning performance describe herein can be employed in various learning contexts between various types of subjects. The term "learner" is generally synonymous with the term "student" as used herein and the term "teacher" is generally synonymous with the entity that is responsible for providing the content for learning by the student and facilitating the learning of the content by the student. Likewise, the term "learning experience," can refer to various learning context or environments and is not limited to conventional educational classroom based learning experiences. For example, the subject learning performance monitoring techniques can be applied to evaluated learning performance of a student in association with participation in a live or recorded lecture, a self-study learning experience, an interactive learning experience, a learning experience involving physical activity, and/or social learning experience, etc. In addition, the subject learning performance monitoring techniques can be employed to monitor learning performance of students in association with participation in an online or virtual classroom experience, wherein the teacher and the student are remotely located.

The terms "mental process" and "mental functioning" are used herein interchangeably to refer to all things that individuals can do with their minds. These include perception, memory, thinking (e.g., such as ideation, imagination, belief, reasoning, etc.), volition, and/or generation or expression of emotion. The term "cognition" can be or include the mental action or process of acquiring knowledge and understanding through thought, experience, and the senses. Cognition can encompass mental processes such as knowledge, attention, memory and working memory, judgment and evaluation, reasoning and computation, problem solving and decision making, comprehension and production of language, etc. A "cognitive state" or "mental state" of an individual can be dynamic and include characteristics of one or more such mental processes. Human cognition can be conscious and unconscious, concrete or abstract, as well as intuitive (e.g., like knowledge of a language) and conceptual (e.g., like a model of a language). Cognitive processes can use existing knowledge and generate new knowledge.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates an example, non-limiting system 100 that facilitates monitoring learning performance using neurofeedback in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

The system 100 and/or the components of the system 100 can be employed to use hardware and/or software to solve problems that are highly technical in nature, that are not abstract and that cannot be performed as a set of mental acts by a human. For example, system 100 and/or the components of the system 100 can be employed to use hardware and/or software to perform operations including monitoring neurofeedback (e.g., haeyomodynamic, metabolic and brainwave data) generated by a student during a learning experience and correlating patterns in the neurofeedback information with qualitative and/or quantitative mental performance measures with respect to one or more defined cognitive function areas. The mental performance measures can be compared to various thresholds to automatically identify if a student is exhibiting low learning performance, thereby facilitating improved processing time for determining if the user is having difficulty learning during a learning experience. In addition, system 100 and/or the components of system 100 can automatically generate and send notifications to the student, the student's teacher, (or another entity responsible for facilitating learning by the student), indicating the student's low learning performance during and/or after the learning experience so that the student and/or the student's teacher can react appropriately. Further, some of the processes performed may be performed by specialized computers for carrying out defined tasks related to the performing affective computing to facilitate automatic provision of auxiliary content to users based on emotional state. System 100 and/or components of the system 100 can be employed to solve new problems that arise through advancements in technology, computer networks, the Internet and the like. System 100 can further provide technical improvements to live and Internet based learning systems by improving processing efficiency among processing components associated with selecting and providing auxiliary information associated with a presentation in real-time based a user's current mental state and preferences.

System 100 can include a plurality of users $104_{1-N}$ (e.g., students or learners) respectively wearing neurofeedback devices $102_{1-N}$ on or around their heads. The neurofeedback devices $102_{1-N}$ can respectively include one or more neuroimaging sensors that continually or regularly capture neuroimaging measurements from one or more areas of the brain representative of mental activity of the brain over the course of engagement or participation of the respective users $104_{1-N}$ in a learning experience, environment or context. The neuroimaging measurements can further be processed to determine one or more characteristics of the cognitive states of the respective users $104_{1-N}$ over the course of engagement or participation of the respective users in the learning experience, environment or context. For example, the learning experience can include attending a live or recorded lecture, participating in a home study session, taking an examination, performing a physical task or experiment, participating in interactive group learning experience, watching or listening to a live or recorded presentation, performance or demonstration, etc. It should be appreciated that the number of users $104_{1-N}$ can vary and that the features and/or functionalities of system 100 can be employed to monitor learning performance of one or more users at a time participating in same or different learning experiences.

In some embodiments, the neurofeedback devices $102_{1-N}$ can perform on-board processing of captured neuroimaging measurements captured by the respective devices. For example, in one implementation, the respective neurofeedback devices $102_{1-N}$ can analyze neuroimaging measurement captured from the respective users and determine one or more characteristics of the respective users' cognitive states. Such characteristics can include for example, quantitative and/or qualitative measures of individual user mental attention level, familiarity level, mental effort level, working memory performance ability, linguistic acquisition ability, social learning ability, and/or mediation ability.

In another implementation, the neurofeedback devices $102_{1-N}$ can further analyze learning information regarding qualitative and/or quantitative cognitive performance in different cognitive function areas to determine an overall learning performance score representative of a user overall learning performance. For example, a overall learning performance score can reflect the user learning performance in each (or, in some embodiments, one or more) of the measured cognitive function areas and indicate on a defined (arbitrary) scale, how well the user is learning and understanding the material being taught (e.g., on a scale of 1 to 10, where a score of 10 indicates the user has fully grasped and understands the material and a score of 1 indicates the user is completely confused and/or has not learned or understood the material at all). According to these embodiments, the neurofeedback devices $102_{1-N}$ can send the processed neuroimaging data to another device for further processing. For example, in the embodiment shown, the other device can include a learning performance server device 106 and/or a teacher device 108. However, in various other embodiments, the neurofeedback devices $102_{1-N}$ can send raw neuroimaging measurements to the learning performance server device 106 as they are captured. The learning performance server device 106 can further process the neuroimaging measurements as they are received (e.g., in real-time or substantially real-time) to determine one or more characteristics of the cognitive states of the respective users $104_{1-N}$ and/or overall learning performance of the respective users $104_{1-N}$ over the course of engagement or participation of the respective users in the learning experience, environment or context.

The learning performance server device 106 can further generate and send notifications based on receiving and/or determining specific learning performance information that has been previously characterized as a triggering event, such as learning performance information representative of a low learning performance level (e.g., relative to a threshold or desired learning performance level). For example, in one or more embodiments, the learning performance server device 106 can generate a notification in response to receiving or determining learning performance information for a user that indicates the user learning performance is below a desired learning performance level. The notification can be generated while the user is participating in the learning experience or after completion of the learning experience. The learning performance server device 106 can further send the notification to a device (e.g., teacher device 108) associated with another entity responsible for facilitating the learning by the student, such as the student's teacher (e.g., teacher 110 or another suitable entity). Accordingly, the student's teacher (e.g., teacher 110) can quickly and effectively address the student learning needs before the student falls further behind. For example, after or while a teacher 110 is teaching conducting a lecture to a plurality of students (e.g., users $104_{1-N}$), the teacher 110 can receive a notification at a device employed by the teacher (e.g., teacher device 108) that identifies one of the students and indicates the student learning performance is low. For instance, the teacher device 108 can include a device associated with the teacher 110 that the teacher can access and/or operate in association with facilitating a learning experiences, such as a desktop computer, a laptop computer, a television, an Internet enabled television, a mobile phone, a smartphone, a tablet user computer (PC), a digital assistant (PDA), a heads up display (HUD), a virtual reality (VR) headset, an augmented reality (AR) headset, or another type of wearable computing device. In some implementations, the notification can include detailed information regarding particular cognitive areas in which the user is exhibiting low learning performance levels, and the particular content or type of content to which the user demonstrated low learning performance levels.

The learning performance server device 106 can also generate and/or store learning performance evaluations for one or more users $104_{1-N}$ and one or more learning experiences of the one or more users. This learning performance information can be accessed and evaluated by the teacher, the user, the user's parents, etc., to track the user learning progress over time. Learning performance information generated for a student or group of students can further be aggregated analyzed (by the learning performance server device 106) to further identify patterns regarding when and why certain students exhibit low learning performance with respect to a type of content being taught, the manner in which the content is taught, the teacher responsible for teaching the content, the duration of the learning experience, the time of day of the learning experience, etc.

The various features and functionalities of the neurofeedback devices described herein (e.g., neurofeedback devices 102) can vary so long as they are capable of capturing neuroimaging measurements (e.g., NIRS measurements and/or EEG measurements) that can be correlated to learning performance with respect to one or more defined cognitive function areas and communicating the raw (or processed) neuroimaging measurements to an external device. For example, in the embodiment shown, the neurofeedback devices $102_{1-N}$ can include one or more bands or straps that rest on or around different regions of the scalp. According to this example embodiment, one or more non-invasive neuroimaging sensors (not shown) can be distributed at different areas on the one or more bands or straps. In other embodiments, the neurofeedback devices $102_{1-N}$ can include a device that is worn as an eyepiece (e.g., glasses, goggles, contacts, etc.), an earpiece, a hat, a patch, etc. so long as the one or more neuroimaging sensors of the device are capable of capturing neuroimaging measurements (e.g., NIRS measurements and/or EEG measurements).

The neurofeedback devices $102_{1-N}$ can further include suitable electrical circuitry to facilitate operation of the one or more neuroimaging sensors. In various embodiments, the neurofeedback devices $102_{1-N}$ can also include suitable communication hardware and software (e.g., a central processing unit (CPU, a transmitter, a transceiver, a decoder/encoder, etc.) to facilitate wired or wireless communication of captured neuroimaging measurements to an external device, such as the learning performance server device 106 and/or teacher device 108. In some embodiments, the neurofeedback devices $102_{1-N}$ can respectively communication raw or processed neuroimaging measurements to external devices respectively associated with the $104_{1-N}$, and the external user devices can forward or relay the raw or processed neuroimaging measurements to the learning performance server device 106.

Figure 2:
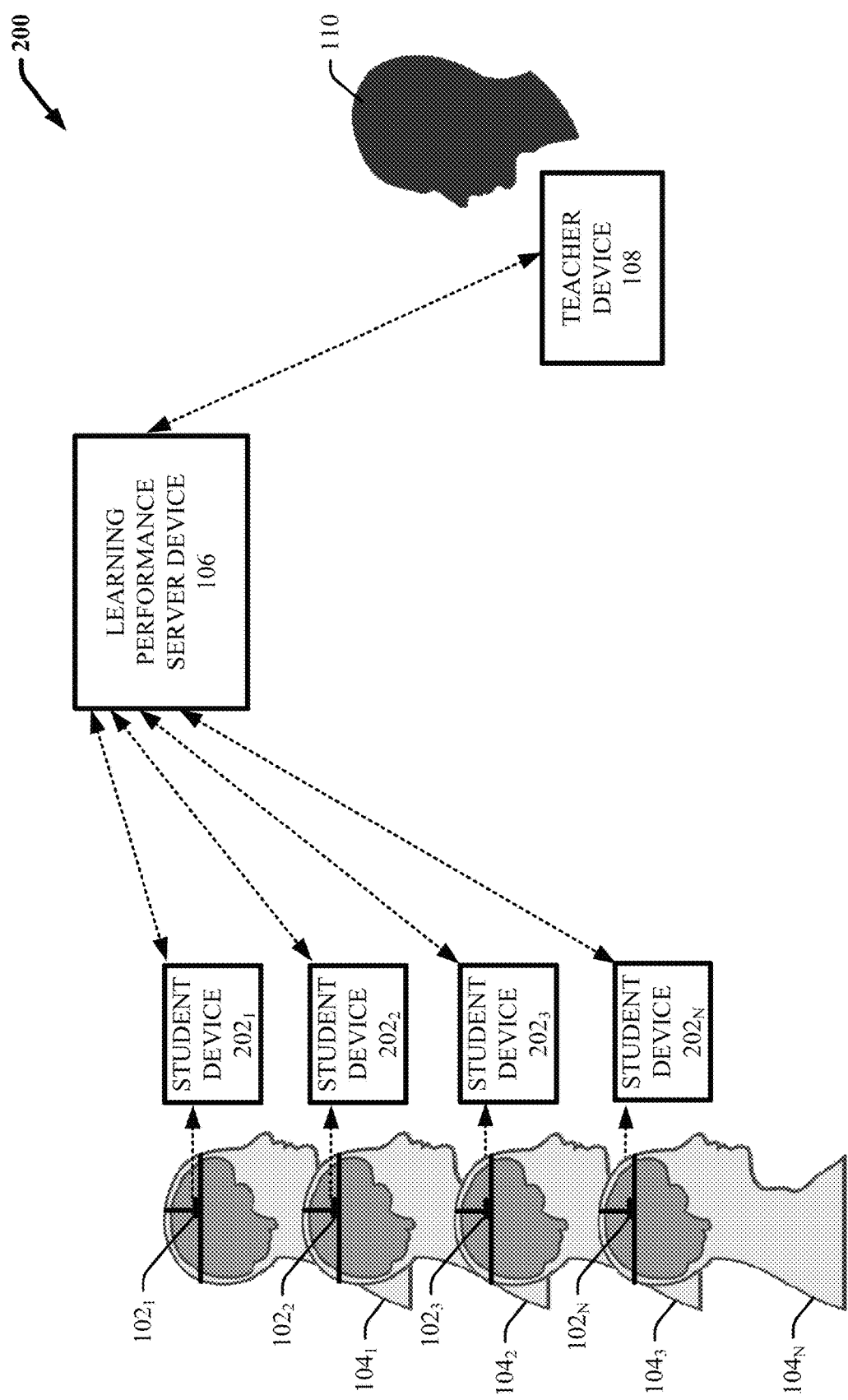
FIG. 2 illustrates another example, non-limiting system that facilitates monitoring learning performance using neurofeedback in accordance with one or more embodiments described herein.

For example, FIG. 2 illustrates another example, non-limiting system that facilitates monitoring learning performance using neurofeedback in accordance with one or more embodiments described herein. System 200 includes same or similar features as system 100 with the addition of one or more student devices $202_{1-N}$. Repetitive description of like elements employed in respective embodiments is omitted for sake of brevity.

In the embodiment shown, each of the users $104_{1-N}$ can be associated with a student device $202_{1-N}$, such as but not limited to, a desktop computer, a laptop computer, a television, an Internet enabled television, a mobile phone, a smartphone, a tablet user computer, a PDA, a HUD, a VR headset, an AR headset, or another type of wearable computing device. In some implementations, the neurofeedback devices $102_{1-N}$ can communicate raw or processed neuroimaging measurements to the student devices $202_{1-N}$ respectively associated with each of the users $104_{1-N}$ using wired communication or a short range wireless communication. In some embodiments, the student devices $202_{1-N}$ can perform some processing of the neuroimaging measurements and further relay the processed neuroimaging information to the learning performance server device 106. In other embodiments, the student devices $202_{1-N}$ can merely relay the raw neuroimaging measurement data to the learning performance server device for processing.

In some embodiments, the learning performance server device 106 can also generate and send notifications to the respective users $104_{1-N}$ at their student devices $202_{1-N}$ regarding their learning performance in association with a learning experience. For example, the learning performance server device 106 can determine if a student is exhibiting low learning performance (e.g., relative to a threshold performance level) and send a notification to the student at the student device 202 associated with the student and informing the student regarding his or her learning performance. The student can then react accordingly in an attempt to improve the student learning performance. For example, in an implementation in which the notification is received during a current learning experience, the student can attempt to re-engage with the experience, take notes, mark the current material for further review after class, ask questions, ask for supplementary material, etc. In another example, in an implementation in which the notification is received after completion of the learning experience, the student can go back through the material taught, ask the teacher or another student for help on the material taught, request more information about the material taught, etc.

With reference to FIGS. 1 and 2, in various implementations, neurofeedback devices $102_{1-N}$, the student devices $202_{1-N}$, the learning performance server device 106 and/or the teacher device 108 can be communicatively coupled via one or more networks (not shown). Such networks can include wired and wireless networks, including, but not limited to, a cellular network, a wide area network (WAN) (e.g., the Internet) or a local area network (LAN). For example, the neurofeedback devices $102_{1-N}$, the student devices $202_{1-N}$, the learning performance server device 106 and/or the teacher device 108 can communicate with one another using virtually any desired wired or wireless technology, including but not limited to: wireless fidelity (Wi-Fi), global system for mobile communications (GSM), universal mobile telecommunications system (UMTS), worldwide interoperability for microwave access (Wi-MAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee® and other 604.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, and/or an ultra-wideband (UWB) standard protocol. For example, in one embodiment of system 100, the neurofeedback devices $102_{1-N}$ can communicate with the learning performance server device 106, and the learning performance server device 106 can communicate with the teacher device 108 via a WAN (e.g., the Internet). In one embodiment of system 200, the student devices $202_{1-N}$ can be respectively associated with the users and $104_{1-N}$ located in relatively close proximity to the users $104_{1-N}$ (e.g., within the same physical classroom space) while the learning performance server device 106 can be located remotely. According to this embodiment, the neurofeedback devices $102_{1-N}$ can communicate with the student devices $202_{1-N}$ using close range wireless communications (e.g., NFC, BLUETOOTH®, etc.) and the student devices student devices $202_{1-N}$ can communicate with the learning performance server device 106 and/or the teacher device 108 using a WAN. As used in this disclosure, the terms "user," "student," "teacher," "presenter," and the like refer to a person, entity, system, or combination thereof that can employ systems described herein (e.g., systems 100, 200 and the like) using a neurofeedback device 102, a student device 202 or a teacher device 108, respectively.

Figure 3:
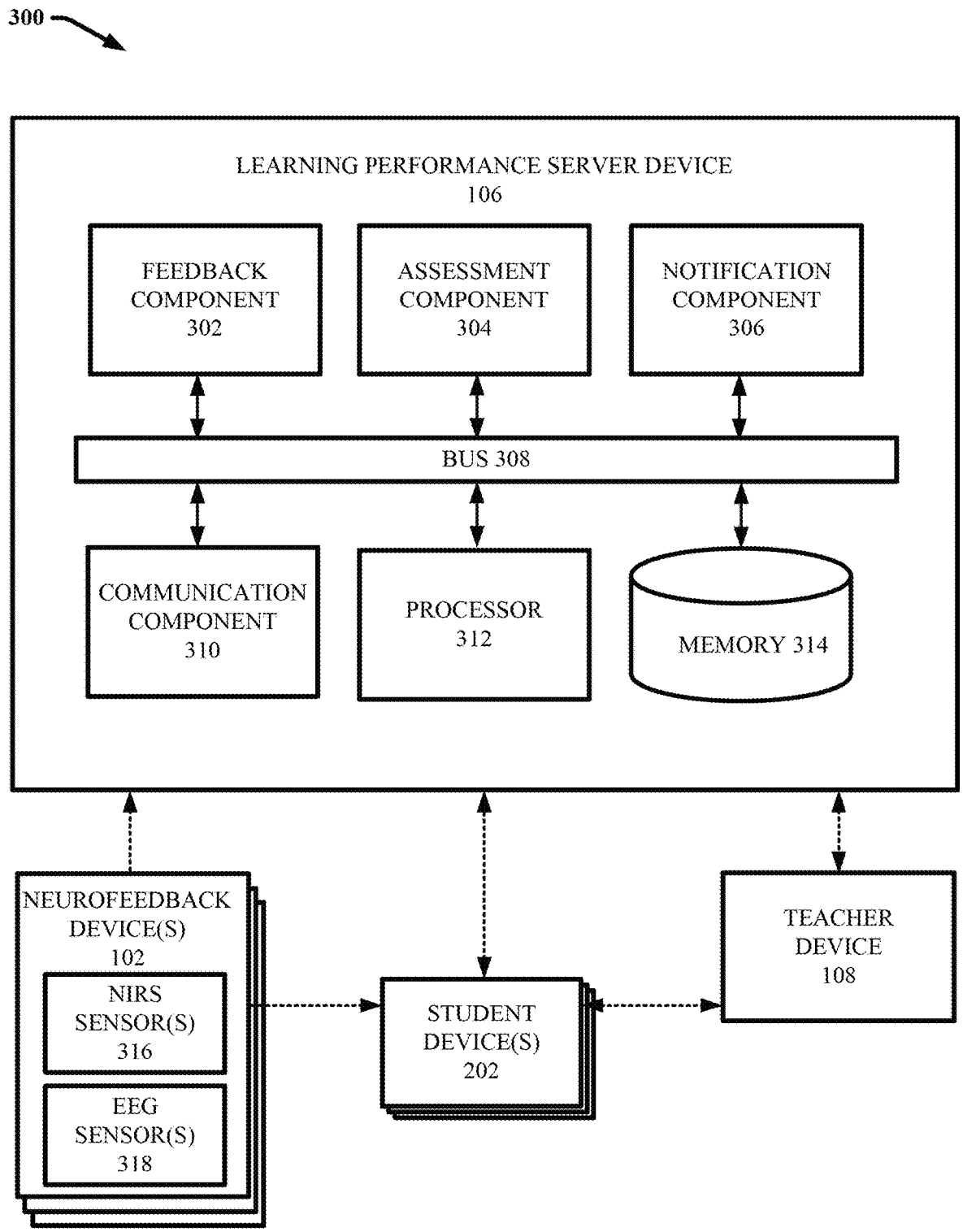
FIG. 3 illustrates a block diagram of an example, non-limiting system that facilitates monitoring learning performance using neurofeedback in accordance with one or more embodiments described herein.

FIG. 3 illustrates a block diagram of an example, non-limiting system 300 that facilitates conditional provisioning of auxiliary information with a media presentation in accordance with one or more embodiments described herein. System 300 can include same or similar features and functionalities as systems 100 and 200 and vice versa. Repetitive description of like elements employed in respective embodiments is omitted for sake of brevity.

As shown in FIG. 3, system 300 can include learning performance server device 106, one or more neurofeedback devices 102, one or more student devices 202 and teacher device 108. The learning performance server device 106 can include various computer-executable components, including, but not limited to, feedback component 302, assessment component 304, notification component 306 and communication component 310. The learning performance server device 106 can also include or otherwise be associated with at least one memory 314 that stores computer-executable components (e.g., the feedback component 302, the assessment component 304, the notification component 306, and the communication component 310). The learning performance server device 106 can also include or otherwise be associated with at least one processor 312 that executes the computer-executable components stored in the memory 314. The learning performance server device 106 can further include a system bus 308 that can couple the various components including, but not limited to, the feedback component 302, the assessment component 304, the notification component 306, the communication component 310, the memory 314 and/or the processor 312.

In order to facilitate monitoring learning performance using neurofeedback, the learning performance server device 106 can include feedback component 302 to receive feedback information regarding mental function of a user in association with participation in a learning experience. In some implementations, the feedback information can be received directly from a neurofeedback device 102 worn by the user. In other implementations, the feedback information can be received from a student device 202 associated with the user, wherein the feedback information or data from which the feedback information was derived (e.g., neuroimaging measurements) was provided by the neurofeedback device 102 to the student device 202. The learning performance server device 106 can include assessment component 304 to analyze the feedback received by the feedback component 302 to determine learning performance information for a user regarding the user learning of content presented to the user in the learning experience. The learning performance server device 106 can further include notification component 306 to generate and send notifications to the user's teacher (e.g., at teacher device 108), to the user (e.g., at the student device 202 of the user), or another suitable entity, based on the learning performance information indicating the user's learning of the content is below a defined learning performance level.

In various exemplary embodiments, the feedback information includes neuroimaging measurements captured via one or more NIRS sensors included on or within a neurofeedback device 102 worn by the user during the learning experience. In some additional embodiments, the feedback can also include neuroimaging measurements captured via one or more EEG sensors included on or within the neurofeedback device 102. For example, in the embodiment shown, the neurofeedback device 102 includes one or more NIRS sensors 316 and one or more EEG sensors. The neurofeedback device 102 can further include the appropriate circuitry to facilitate operation of the one or more NIRS sensors (e.g., light emitters, light detectors, etc.,) and the one or more EEG sensors (e.g., electrodes and conductive wiring). In various embodiments, the neurofeedback device 102 can also include suitable communication hardware and software (e.g., a transmitter, transceiver, etc.) to facilitate wired or wireless communication of captured neuroimaging measurements to an external device, such as the learning performance server device 106, the student device 202 and/or teacher device 108.

NIRS is a spectroscopic method that uses the near-infrared region of the electromagnetic spectrum (from about 700 nanometer (nm) to 2500 nm). The primary application of NIRS to the human body uses the fact that the transmission and absorption of NIR light in human body tissues contains information about hemoglobin (Hb) concentration changes. Functional near-infrared spectroscopy (fNIRS) is a haemodynamic neuroimaging technology that indirectly measures neuronal activity in the cortex of the brain via neuro-vascular coupling. fNIRS works by quantifying Hb concentration changes in the brain based on optical intensity measurements, measuring the same hemodynamic changes as functional magnetic resonance imaging (fMRI). The most commonly used form of fNIRS uses infrared light, introduced at the scalp, to measure changes in blood oxygenation as oxygenated-Hb converts to deoxygenated-Hb during neural activity (e.g., the cerebral haemodynamic response). fNIRS uses specific wavelengths of light to provide measures of cerebral oxygenated and deoxygenated Hb that are correlated with the fMRI blood-oxygenation-level-dependent (BOLD) signal.

For example, in various embodiments, the neurofeedback device 102 can have a configuration such that one or more NIRS sensors 316 are placed at one or more locations around the head of a user, including but not limited to: the prefrontal cortex (PFC), the lateral prefrontal cortex (LPFC), the bilateral ventral lateral prefrontal cortex (VLPFC), and the medial and lateral orbitofrontal cortex (OFC). The NIRS sensors 316 can thus capture hemodynamic measurements from different regions of the brain, allowing for determining characteristics of the subjects cognitive state through the use of pattern classification. For example, in various embodiments, the one or more NIRS sensors 316 can capture neuroimaging measurements including changes in oxygenated-Hb levels in the different areas of the brain by measuring changes in the concentration of oxygenated and deoxygenated-Hb as well as the changes in the redox state of cytochrome-c-oxidase (Cyt-Ox) by their different specific spectra in the near-infrared range between 700-1000 nm. These neuroimaging measurements can further be provided to the feedback component 302 as they are captured (e.g., in real-time or substantially real-time) to facilitate assessment of the cognitive state of the user during or after participation in the learning experience (e.g., via assessment component 304).

In some embodiments, fNIRS can provide an attractive method for continuous monitoring of brain dynamics fNIRS is safe, highly portable, user-friendly and relatively inexpensive, with rapid application times and near-zero run-time costs.fNIRS also offers a compromise between the spatial resolution of fMRI and temporal resolution of EEG. The superior spatial resolution (localization of activation) of fNIRS relative to EEG allows for greater accuracy in identifying specific brain regions responding to changes in workload. The superior temporal resolution (higher sampling rate) of fNIRS relative to fMRI affords improved statistical power when analyzing changes in the shape of the hemodynamic response.

The electroencephalogram or electroencephalography (EEG) is an electrophysiological monitoring method to record electrical activity of the brain. It is typically noninvasive, and uses one or more EEG sensors 318 (e.g., electrodes) placed along the scalp. EEG measures voltage fluctuations resulting from ionic current within the neurons of the brain. Scalp EEG activity shows oscillations at a variety of frequencies. Several of these oscillations have characteristic frequency ranges, spatial distributions and are associated with different states of brain functioning. Voltage fluctuations are measured at multiple sites on the scalp using electrodes that make resistive or capacitive contact to the subject. Example brain signals are EEG data, event-related potentials (ERP) and other brain electrical responses that are manifest in the time and/or frequency domain. Patterns in EEG measurements have been successfully related to mental activity associated with levels of attention, familiarity, mental effort, working memory, linguistic acquisition, social learning, and mediation levels. In various embodiments, the one or more EEG sensor can capture measurements associated with but not limited to: mu waves, theta waves, delta waves, beta waves, alpha waves, gamma waves, and waves associated with homologous frontal brain sites.

In some embodiments, in addition to neurofeedback captured via one or more neuroimaging sensors (e.g., NIRS sensors 316 and/or EEG sensors 318), the feedback component 302 can further receive feedback associated with facial expressions and/or body language of the user that can be correlated to characteristics of the mental state of the user. For example, system 300 can employ various existing emotion/mental state recognition technologies that can determine a user mental or emotional state based on analysis of facial expressions, eye movement, and/or body language of the user captured in video or one or more images of the user. With facial emotion detection, algorithms can detect faces within a photo or video, and sense micro expressions by analyzing the relationship between points on the face, based on curated databases compiled in academic environments. According to these embodiments, the neurofeedback device 102, the student device 202 or another device (not shown) can capture video or image data of the user during participation in the learning experience. For example, in some embodiments, the neurofeedback device 102 or the student device 202 can include a HUD device including a user facing camera or image sensor that can capture facial expressions and/or eye movements of the user during a learning experience. In another example, a user facing camera can be included on a device such as a tablet, smartphone, desktop or laptop computer employed by the user and capture facial expressions and/or eye movements of the user during a presentation. In another example, an external user facing camera can be included in a same room as the user or a group of users and capture facial expressions and/or eye movements of the respective users. In some implementations, motion data that can be correlated to body language (e.g., gestures, fidgeting, remaining relatively still, changing a body position, blinking, foot tapping, etc.) and further correlated to mental states of the user can be captured via one or more motion sensors worn by the user. For example, the one or more motion sensors can be included on or within the neurofeedback device 102, the student device 202 or another device. In one implementation, the neurofeedback device 102, the student device 202 or the other device can further send the image data and/or motion data to the feedback component 302 for processing by the assessment component 304 to determine mental state characteristics based on detected facial expressions, eye movements and/or body language. Alternatively, the neurofeedback device 102, the student device 202 or the other device can process the image data and/or motion data and send processed information mental state characteristics of the user to the feedback component 302.

The assessment component 304 can analyze feedback received from the feedback component 302 regarding mental functioning of a user (e.g., neuroimaging feedback, facial expression feedback and/or body language feedback) in association with participation in a learning experience to determine various characteristics about the learning performance of the user. For example, the assessment component 304 can identify patterns in received neuroimaging measurements that correlate to defined quantitative and/or qualitative performance levels with respect to defined cognitive function areas, including but not limited to: attention, familiarity, mental effort, working memory, linguistic acquisition, social learning, and mediation. In particular, in embodiments in which the feedback component 302 receives neuroimaging measurements from one or more NIRS sensors positioned at defined areas on a student's scalp, the neuroimaging measurements can include changes in oxygenated-Hb levels in the different areas of the brain over time. The assessment component 304 can identify patterns in the changes in the oxygenated-Hb levels in the different areas of the brain over time that have been previously associated with information accessible to the assessment component 304 (e.g., stored in memory 314) correlating the patterns to performance levels of different cognitive states, including workload and mental stress, working memory performance and attention.

For example, the assessment component 304 can determine a level or degree of mental workload or stress of a user based on the amount and degree of increase in oxygenated-Hb in defined areas of the brain over time. Various studies have shown a linear relationship between task workload and haemodynamics where the difficulty of the task at hand does not exceed the cognitive capacity of participant. In particular, these studies have found a linear correlation between an increase in workload or mental stress and an increase in oxygenated-Hb in various regions in the brain (e.g., the left medial/orbito frontal cortex and the bilateral ventral lateral prefrontal cortex (PFC)). In addition, the presence of a negative quadratic slope during fNIRS monitoring of workload dynamics has been found to be indicative of task overload. Further, increase in mental stress or effort has been observed based on asymmetry of oxygenated-Hb levels in the left and right hemispheres of the PFC.

In another example, the assessment component 304 can determine a level or degree of working memory performance based on the amount and/or degree of increase in oxygenated-Hb in defined areas of the brain over time. Working memory refers to the process of actively maintaining relevant information for defined periods of time. Working memory is a key function for various cognitive processes such as planning and reasoning, and these processes are important for intellectual work. Furthermore, working memory performance is higher in healthy individuals compared with patients with certain psychiatric disorders, such as schizophrenia, depression, and bipolar disorder. Various studies have shown that better working memory performance is correlated with elevated oxygenated-Hb levels (e.g., with respect to a threshold or baseline level) in the LPFC. In addition, the assessment component 304 can determine a level or degree of user attention based on comparison of levels of oxygenated-Hb in the right and left hemispheres of the PFC relative. In particular, increased attention levels have been observed when the amount of oxygenated-Hb in the right hemisphere is greater than that of the left hemisphere.

Further, in embodiments in which the feedback component 302 receives neuroimaging measurements from EEG sensors positioned at defined areas on a student's scalp, the neuroimaging measurements can include brain waves generated from different areas of the brain over time. The assessment component 304 can further identify patterns in brain waves generated from different areas of the brain over time that have been previously associated within information accessible to the assessment component 304 (e.g., stored in memory 314) correlating the patterns to performance levels of different cognitive states, including but not limited to: attention, familiarity, mental effort, working memory, linguistic acquisition, social learning, and mediation. For example, the assessment component 304 can determine user attention levels based on patterns in the ratio of theta to beta waves, wherein inattentiveness is reflected by greater theta activity. In another example, the assessment component 304 can determine information regarding attention levels and memory retention based on patterns in gamma waves. In another example, the assessment component 304 can determine information regarding working memory based on patterns in theta waves. In another example, the assessment component 304 can determine information regarding linguistic acquisition based on delta activity. In another example, the assessment component 304 can determine information regarding active thinking based on beta activity. In another example, the assessment component 304 can determine information regarding social learning, based on mu rhythms and arousal based on observation of hemispheric frontal alpha asymmetry (HFAA).

Accordingly, based on observed patterns in neuroimaging measurements received from a user in association with participation in a learning experience, the assessment component 304 can determine learning performance information for the user regarding the user's learning of content presented to the user in the learning experience. In some embodiments, the learning information can include values representative of the quantitative and/or qualitative cognitive performance of the user with respect to one or more of the defined cognitive function areas (e.g., attention, familiarity, mental effort, working memory, linguistic acquisition, social learning, and mediation). For example, with respect to an arbitrary scale wherein a score of 1 indicates extremely poor performance and 10 indicates extremely high performance, based on patterns in received neuroimaging data, the assessment component 304 can determine a user attention level is an 8, familiarity level is 6, mental effort level is a 6, working memory level is a 7, linguistic acquisition level is a 6, etc. The assessment component 304 can further determine a general or overall learning performance score representative of the user's learning of content associated with the received feedback based on performance scores in each of the defined cognitive function areas. In some embodiments, performance scores in the respective cognitive function areas can be weighted based on a predetermined degree to which the respective cognitive function areas represent overall learning performance with respect to the particular learning experience and/or content being taught. For example, in association with evaluating learning performance with respect a learning experience that involves a significant amount of reading comprehension, working memory functioning can be weighted higher than social learning or mediation. It should be appreciated that other scales and scoring mechanisms can be used to value learning performance with respect to different cognitive function areas and that the particular cognitive function areas that are evaluated can vary based on the type of learning experience and the cognitive areas considered relevant to the type of learning experience, academic institution, the student, the teacher, etc.

In some embodiments, the assessment component 304 can analyze all the feedback received for a user during a learning experience after completion of the learning experience to evaluate the student learning performance for the learning experience. For example, after the learning experience is completed, the assessment component 304 can determine learning performance scores for a user in each evaluated cognitive function area that reflect the user average learning performance in each cognitive function area. In another example, after the learning experience is completed, the assessment component 304 can determine a single overall learning performance score representative of the user overall learning performance with respect to the learning experience based in part on the user average performance in one or more of the cognitive function areas.

In other embodiments, the assessment component 304 can continually or regularly analyze feedback received for a user over the course of the learning experience to monitor the user's learning performance over the course of the learning experience. The assessment component 304 can further identify feedback indicative of poor learning performance as soon as it is received (e.g., in real-time) so that the notification component 306 can notify the user, the user's teacher, or another suitable entity immediately. In particular, the assessment component 304 can determine, based on one or more patterns in received neuroimaging measurements over time, if a student demonstrates a low learning performance state in one or more of the defined cognitive function areas and/or if a student demonstrates a low learning performance in general based on combined scores for two or more defined cognitive function areas. For example, the assessment component 304 can determine that a user's working memory performance level is currently below a desired performance level based on received neurofeedback measurements indicating the level of oxygenated-Hb in the LPFC region of the user's brain has remained below a defined level for over a defined period of time. In another example, the assessment component 304 can determine that a user's overall learning performance is currently below a desired performance level based on received neurofeedback measurements indicating the user's performance in two or more combined cognitive function areas reflects an overall learning performance score that is below a threshold overall learning performance score.

The notification component 306 can further generate notifications based on a user learning performance results. In particular, in various embodiments, the notification component 306 can generate a notification based on a determination, by assessment component 304, that a student learning performance is below a desired performance level (e.g., with respect to a threshold performance level or score). For example, the notification component 306 can generate a notification based on a determination that a user overall learning performance score is below a threshold learning performance score, either during the learning experience or after the learning experience. In another example, the notification component 306 can generate a notification based on a determination that a user's learning performance in a particular cognitive function area is below a desired level, either during the learning experience or after the learning experience.

The information included in a notification can vary. In some embodiments, the notification can identify the student and state generally that the student's performance level is below a desired performance level. For example, the notification component 306 can generate a notification that states "Erin is struggling with this material." In other embodiments, the notification can provide a measure or score that represents the user's low performance level. For example, the notification component 306 can generate a notification that states "Erin's learning performance level is currently at about 50% relative to the desired level of 75% or higher." In another embodiment, the notification can identify the one or more defined cognitive function areas that the user is exhibiting a low performance level in and/or provide measures or scores representative of the specific performance levels observed in each of the cognitive function areas. For example, the notification component 306 can generate a notification that states "Erin's attention level is currently about a level 5 and her working memory performance is at about a level 4," wherein the recipient of the notification has knowledge of the significance of the scoring mechanism.

In various embodiments, the notification component 306 can further send the notifications to the student (e.g., at the student's student device 202), the student's teacher (e.g., at the teacher device 108), or another suitable entity (e.g., the student's parent, tutor, etc.), in response to generation of the notification. According to these embodiments, the student, the student's teacher, or the other suitable entity can receive notifications regarding low student performance as soon as it is detected (e.g., via assessment component 304). For example, in embodiments in which the assessment component 304 regularly or continuously determines when a user's learning performance falls below a desired level throughout a learning experience, the notification component 306 can generate and send a notification regarding the user's drop in learning performance during the learning experience (e.g., as soon as the drop in performance occurs and is detected by assessment component 304). In another example, in embodiments in which learning performance evaluation is performed by the assessment component 304 after completion of the learning experience, the notification component 306 can generate and send a notification regarding the user learning performance for the learning experience as soon as the learning experience is completed. By receiving real-time or substantially real-time notifications regarding learning performance during or immediately following a learning experience, the student, the teacher, or the other suitable entity can react accordingly in attempts to improve the student learning performance and/or understanding of the content being taught before becoming too far behind.

In other embodiments, one or more notifications generated for a student can be stored in a queue and accessed by the student, the student's teacher, or the other suitable entity, on demand. In some implementations, the notification component 306 can alert the student, teacher, or other suitable entity when a notification has been generated regarding the student's low learning performance. The student, teacher or other suitable entity can then request and receive the full notification when appropriate. For instance, while teaching a class, a teacher can receive alert messages at the teacher's teacher device indicating when a student is exhibiting low learning performance and indicating that a notification with more information regarding the student learning performance has been generated. In some embodiments, the alert messages can identify the particular students exhibiting the low learning performance. The teacher can then review the notifications on a break period and address the students learning issues after or during the break period.

The communication component 310 can facilitate wireless communication between the learning performance server device 106, and the one or more neurofeedback devices 102, the one or more student device 202, the teacher device 108, or another suitable external device (not shown). For example, the communication component 310 can receive feedback information from neurofeedback device 102, and/or student devices 202 regarding the mental functioning/activity of a user during a learning experience. In another example, the communication component 310 can send notification messages and/or alert messages to the one or more student device 202, the teacher device 108 and/or another suitable device. The communication component 310 can be or include hardware (e.g., a central processing unit (CPU), a transceiver, a decoder), software (e.g., a set of threads, a set of processes, software in execution) or a combination of hardware and software that facilitates the various type of wireless communicating information of information described herein.

It should be appreciated that the architecture of system 300 can vary. For example, although various components of system 300 (e.g., the feedback component 302, the assessment component 304, and the notification component 306) are provided on a server device (e.g., a learning performance server device 106), in other embodiments, any number of different types of devices can be associated with or include the aforementioned components. All such embodiments are envisaged. For example, one or more of the components included at the learning performance server device 106 can be located at another device, such as the neurofeedback device 102, the student device 202, and/or the teacher device 108. Still in other embodiments, one or more components, features and functionalities of the neurofeedback device 102, the student device 202 and/or the learning performance server device 106 can be combined. For example, in one embodiment, a system is envisioned wherein the features and functionalities of the learning performance server device 106 are provided on the student device 202 and the learning performance server device 106 is removed from the system. According to this embodiment, the neurofeedback device 102 can provide neuroimaging feedback and possibly image and motion data feedback (e.g., captured via a camera and/or motion sensor) regarding the mental functioning of the user to the user's student device 202. The student device 202 can further include suitable hardware and software that facilitates processing the feedback, generating notifications and alerts regarding low learning performance levels, providing or sending the notifications and alerts to the student or the student's teacher, reviewing monitored learning performance information over time, etc. Still in yet another embodiment, the features and functionalities of the neurofeedback device 102, the student device 202 and the learning performance server device 106 can be included in a single device worn by the user.

Figure 4:
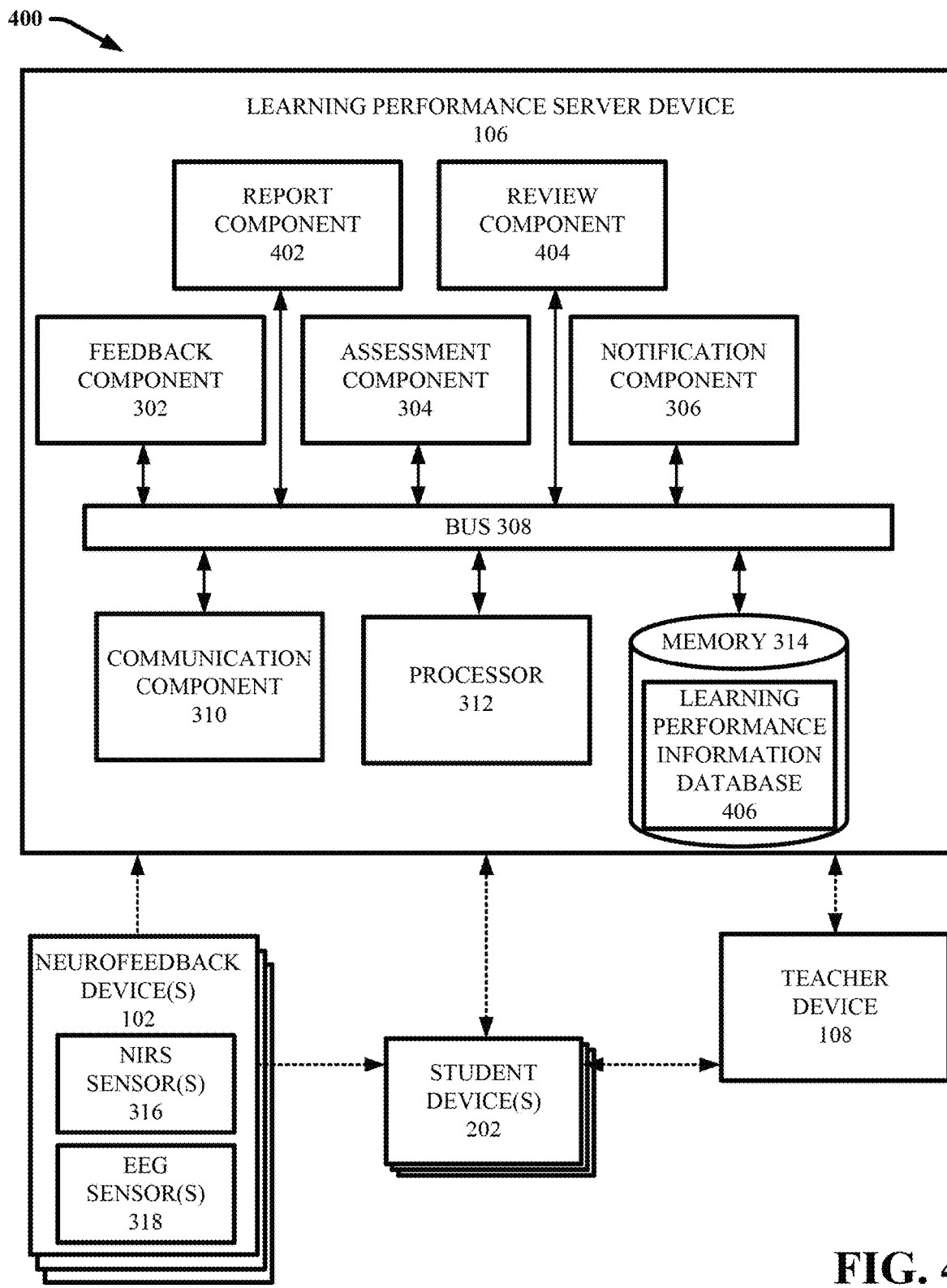
FIG. 4 illustrates a block diagram of another example, non-limiting system that facilitates monitoring learning performance using neurofeedback in accordance with one or more embodiments described herein.

FIG. 4 illustrates a block diagram of another example, non-limiting system 400 that facilitates monitoring learning performance using neurofeedback in accordance with one or more embodiments described herein. System 400 can include the same or similar features as system 300 with the addition of report component 402, review component 404 and learning performance information database 406 to the learning performance server device 106. Repetitive description of like elements employed in respective embodiments is omitted for sake of brevity.

In various embodiments, in addition to generating notifications regarding student learning performance (particularly notifications regarding low or poor student performance), the learning performance server device 106 can include report component 402 to generate and store learning performance assessment information that evaluates a student's collective learning performance for a given learning experience. For example, the learning performance information for a student can be in the form of a report that includes a summary of the assessment of the student learning performance for a given learning experience. The report component 402 can further generate and store learning performance evaluations or reports for a student for various learning experiences the student participates in over time. In addition, the report component 402 can generate learning performance for each student that participates in a particular learning experience (e.g., each student in the class). The learning performance reports or assessments can be collected and stored by the learning performance server device 106 in a learning performance information database 406 (e.g., in memory 314). The learning performance information database 406 can also store notifications generated by the notification component 306.

The information included in a learning assessment report can vary depending on the assessment capabilities of the assessment component 304. In some embodiments, a learning assessment report can include information identifying an overall learning performance score for a student with respect to a particular learning experience. In another embodiment, the report can include average learning performance scores for the student with respect to each monitored cognitive function area. In another embodiment, the assessment component 304 can regularly or continuously determine a student's average learning performance score or learning performance scores in respective cognitive function areas at different points in time throughout a learning experience. According to this embodiment, the learning assessment report can include a graph that charts the student learning performance scores over time for the duration of the learning experience. In another embodiment, a learning assessment report can include information indicating whether and when low learning performance was observed over the course of a learning experience and what cognitive function areas the low learning performance was observed in. In some embodiments, the reports can include notification information. For example, a learning assessment report can identify the number of low learning performance notifications generated, the scores associated with the low learning performance notifications, the cognitive function areas associated with the low learning performance notifications, and the time when a notification was generated (e.g., point or period of time in the learning experience). The learning assessment report can also include the actual notifications or links to the actual notifications.

The review component 404 can facilitate reviewing learning performance assessments or reports and notifications stored in the learning performance information database 406. For example, the review component 404 can allow a student, the student's teacher, or another suitable entity to access, review, and/or download learning performance evaluations/reports and/or notifications for the student stored within the learning performance information database 406. In some embodiments, the communication component 310 can send generated reports to the student (e.g., at the student device 202 of the student), the student's teacher (e.g., as the teacher device 108), or another suitable entity (e.g., the student's parent, tutor, etc.) in response to generation of the reports by the report component 402. Accordingly, the student, the student's teacher, the student's parent, etc., can regularly track the student's learning progress over time to determine whether the student is improving or falling behind, and/or to determine what cognitive performance areas the student needs to work. In addition, the teacher can access reports generated for a group of students associated with a same learning experience (e.g., a same class, a same lecture, etc.) and can compare the learning performances of students relative to one another to determine collectively how the respective student learning performance varies. For example, the teacher can go back and look at the collective learning performance feedback for a class as a whole to learn how the students react to specific tasks (e.g., like lecture, individual work, small group work, exams, etc.) and adjust their lesson plans accordingly to try and make their time with the students more effective. For instance, the teacher can determine whether most students struggled with the material or just a small subset of the students. In another example, the teacher can determine whether most students had trouble focusing on the lesson or whether just a few of the students had trouble. In another example, the teacher can determine what material the students find particularly difficult, interesting, easy, etc., and adjust their curriculum or teaching techniques accordingly.

In some embodiments in which a video and/or audio recording of the learning experience is captured, the video or audio recording can also be provided to and stored by the learning performance server device 106. According to these embodiments, the review component 404 can also facilitate reviewing learning performance reports in association with the recorded video and/or audio. For example, the review component 404 can facilitate streaming of the video and/or audio recording of the learning experience to the teacher device 108 in association with review of learning performance information generated for one or more students participating in the learning experience. The teacher can thus manually review what the information was being presented when students exhibited low learning performance in various cognitive areas and determine when and why some students may have demonstrated low learning performance. The teacher can then adapt her teaching techniques and curriculum accordingly.

Figure 5:
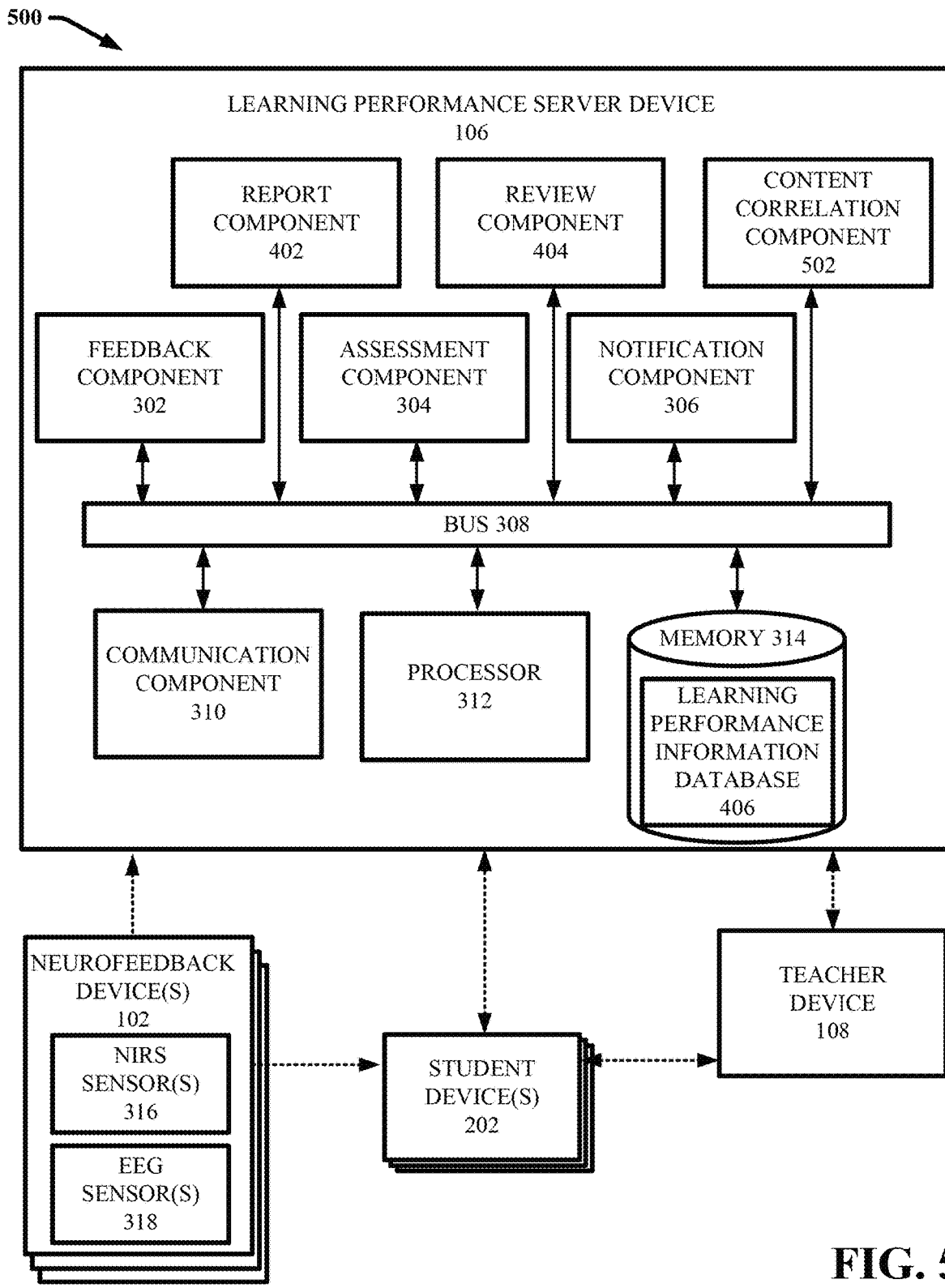
FIG. 5 illustrates a block diagram of another example, non-limiting system that facilitates monitoring learning performance using neurofeedback in accordance with one or more embodiments described herein.

FIG. 5 illustrates a block diagram of another example, non-limiting system 500 that facilitates monitoring learning performance using neurofeedback in accordance with one or more embodiments described herein. System 500 can include same or similar features as system 400 with the addition of content correlation component 502 to the learning performance server device 106. Repetitive description of like elements employed in respective embodiments is omitted for sake of brevity.

As described above, in some embodiments, the review component 404 can facilitate manually reviewing a video and/or audio recording of a learning experience to correlate different content being discussed and/or presented with low student learning performance feedback. In other embodiments, the learning performance server device 106 can include content correlation component 502 to automatically correlate content being discussed or presented in a learning experience with low learning performance feedback to automatically identify the particular content a student struggled with. Once the content correlation component 502 has determined a particular part of the content included in the learning material that was being presented or discussed during a learning experience when low learning performance was observed, the content can further be identified in a low learning performance notification or learning performance assessment report.

In particular, the content correlation component 502 can automatically correlate feedback indicating a low learning performance with a specific part of the content included in the learning experience that was being presented or discussed at the time the feedback was received. For instance, in one or more embodiments, the learning performance server device 106 can have access to information identifying content included in a learning material, such as a presentation, a lecture, an exam, etc., (e.g., in memory 314 or at another device). For example, in embodiments in which the presentation is a live presentation, the learning performance server device 106 can have access to information that identifies different topics and/or sub-topics included in the presentation and content respectively associated with the different topics and/or sub-topics. In another example in which the presentation includes a live or recorded presentation that includes a slideshow, the learning performance server device 106 can have access to information identifying content included in respective slides of the slideshow and/or content associated with different parts or elements of a single slide.

In some embodiments, the content correlation component 502 can determine a part of the content included in a presentation that is associated with reception of user feedback based on timing of reception of the feedback and a current time point or time frame associated with the presentation. For example, the presentation can include a live or recorded presentation associated with a known duration wherein particular parts or content included in the presentation are associated with known time points or time frames over the duration of the presentation. For example, with respect to a presentation including a plurality of known topics identified as topic 1, topic, 2, topic 3, etc., each (or, in some embodiments, one or more) of the different topics can be associated with known time points or time frames throughout the presentation. Information regarding content respectively associated with different time points or time frames of the presentation can be stored in memory 314 or otherwise accessible to the content correlation component 502. Accordingly, as a presentation is being presented, the content correlation component 502 can determine a time point or time frame of the presentation associated with reception of the feedback. For example, in some implementations, the learning performance server device 106 can receive information identifying the start time of the presentation and track the presentation time following the start of the presentation. In another example, in implementations in which the presentation includes a video, the learning performance server device 106 can receive information identifying a current time in the video when the feedback is received. In some embodiments, the learning performance server device 106 can play the video or stream the video to the user's user device (e.g., student device 202) and thus correlate received feedback with a current time point or time frame of the video. The content correlation component 502 can further identify the particular content of the presentation (e.g., topic 1, topic, 2, topic, 3, etc.) associated with that time point or time frame.

In another embodiment in which the presentation includes a slideshow, the content correlation component 502 can have access to information (e.g., stored in memory 314 or at another device) identifying content of the presentation respectively associated with each slide (or, in some embodiments, one or more slides). The content correlation component 502 can further determine or receive information identifying a current slide that is being presented during a presentation at a time when the feedback is received. For example, in some embodiments, the learning performance server device 106 can provide or render the respective slides and thus have direct knowledge about what slide is currently being presented. In some implementations, the content correlation component 502 can further have access to information identifying sub-topics or elements in a same slide and determine the particular sub-topic or element of a same slide that is being presented at the time feedback is received. For example, the slides can include interactive slides in which different elements or parts of a single slide can be activated or highlighted. According to this implementation, the content correlation component 502 can determine the particular sub-topic or element being presented at the time feedback is received based on information indicating a particular part or element of the slide is being pointed to, highlighted, selected or otherwise activated.

Still in other embodiments, the learning performance server device 106 can include or have access to information associating known keywords in a presentation with specific parts of the content of the presentation. According to these embodiments, the feedback component 302 can receive or determine information identifying a known keyword that is spoken during the presentation at a time associated with reception of the feedback. For example, the content correlation component 502 can include or employ speech recognition hardware and software to identify keywords spoken throughout the presentation included in an audio recording of the presentation. The content correlation component 502 can further determine a keyword (or keywords) spoken at time associated with reception of the feedback and further correlate the feedback with the known part of the content associated with the keyword (or keywords).

Figure 6:
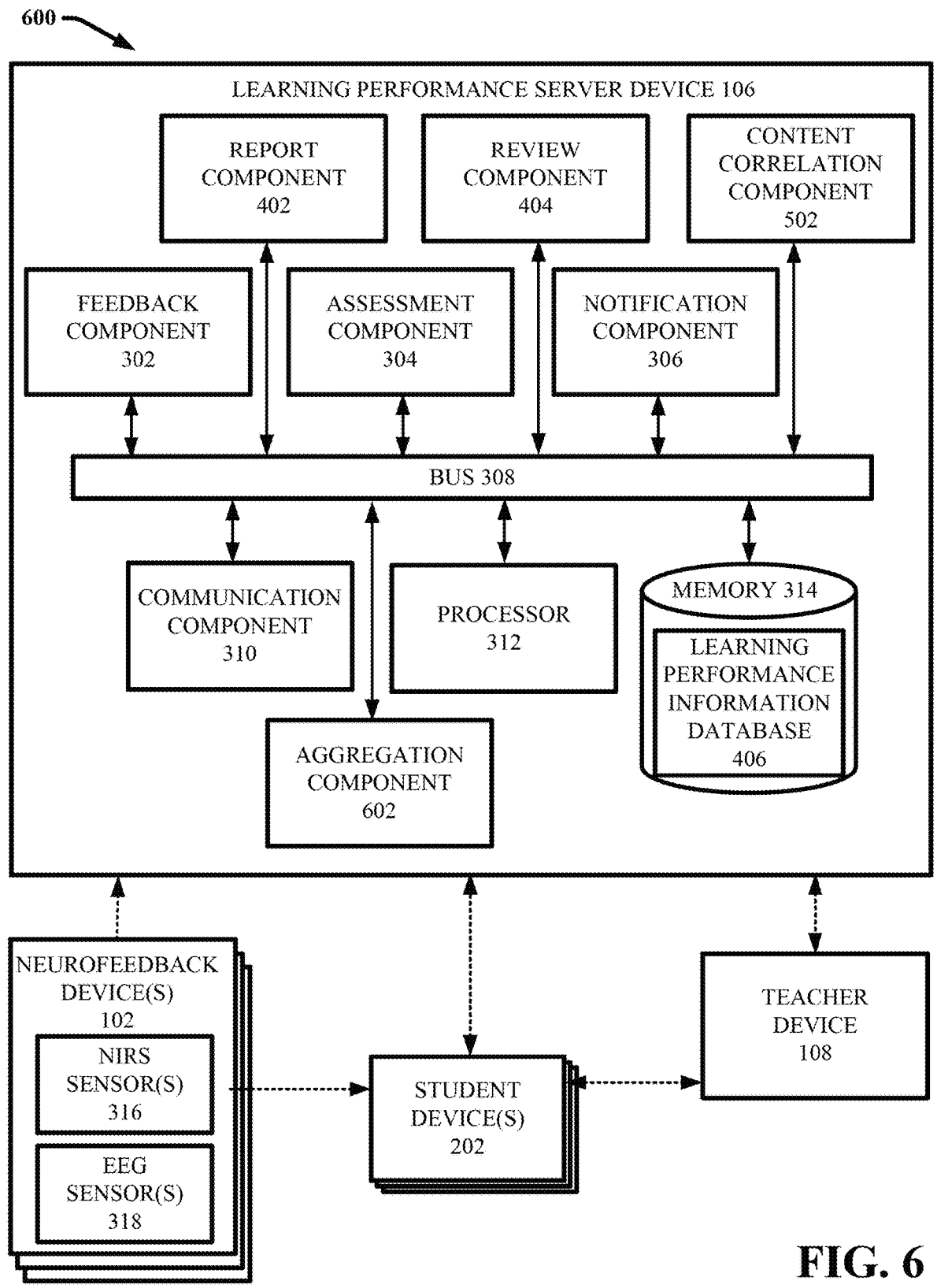
FIG. 6 illustrates a block diagram of another example, non-limiting system that facilitates monitoring learning performance using neurofeedback in accordance with one or more embodiments described herein.

FIG. 6 illustrates a block diagram of another example, non-limiting system 600 that facilitates monitoring learning performance using neurofeedback in accordance with one or more embodiments described herein. System 500 can include same or similar features as system 400 with the addition of aggregation component 602 to the learning performance server device 106. Repetitive description of like elements employed in respective embodiments is omitted for sake of brevity.

In some embodiments, the learning performance server device 106 can include aggregation component 602 to aggregate learning performance information generated for a single student or a group of students over time. The aggregation component 602 can further analyze the aggregated learning performance information to identify and predict various types of information that can be used to evaluate and improve student learning performance. For example, in one implementation, the aggregation component 602 can aggregate learning performance information for a single student generated in associating with participation of the student in learning experiences associated with different learning experiences over time, different types of learning experiences, different teachers, different subjects, different types of content, different durations of learning experiences, different times of day of the learning experiences, different academic institutions providing the learning experiences, etc. The aggregation component 602 can further process the aggregated information using root cause analysis techniques to identify patterns in the information regarding the user's learning performance. For example, the aggregation component 602 can identify factors that tend to contribute to low learning performance in general and/or low learning performance in certain cognitive function areas, including but not limited to: the type of learning experience, the teacher, the subject, the type of content, duration of the learning experience, the time of day of the learning experience, the academic institution providing the learning experience, etc. The aggregation component 602 can further aggregate learning performance information for different students with respect to the various areas described above to further identify correlations between common factors associated with poor learning performance. For example, the aggregation component 602 can identify certain types of learning experiences, certain types of subject, certain types of content, etc., that many students tend to demonstrate low learning performance levels towards. The aggregation component 602 can further regularly track learning performance progress of students after various changes to teaching methods have been adopted to determine whether the changes contributed to improved learning performance. Likewise, the aggregation component 602 can identify certain teachers or teaching methods that contribute to low learning performance levels and track the performance of the teachers over time with respect to their ability to facilitate improving the learning performance of their students.

In order to provide for or aid in the numerous inferences described herein, the aggregation component 602 can examine the entirety or a subset of the data to which it is granted access and can provide for reasoning about or infer states of the system (e.g., system 600 and the like), environment, etc. from a set of observations as captured via events and/or data. An inference can be employed to identify a specific context or action, or can generate a probability distribution over states, for example. The inference can be probabilistic (e.g., the computation of a probability distribution over states of interest can be based on a consideration of data and events). An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x4, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 7:
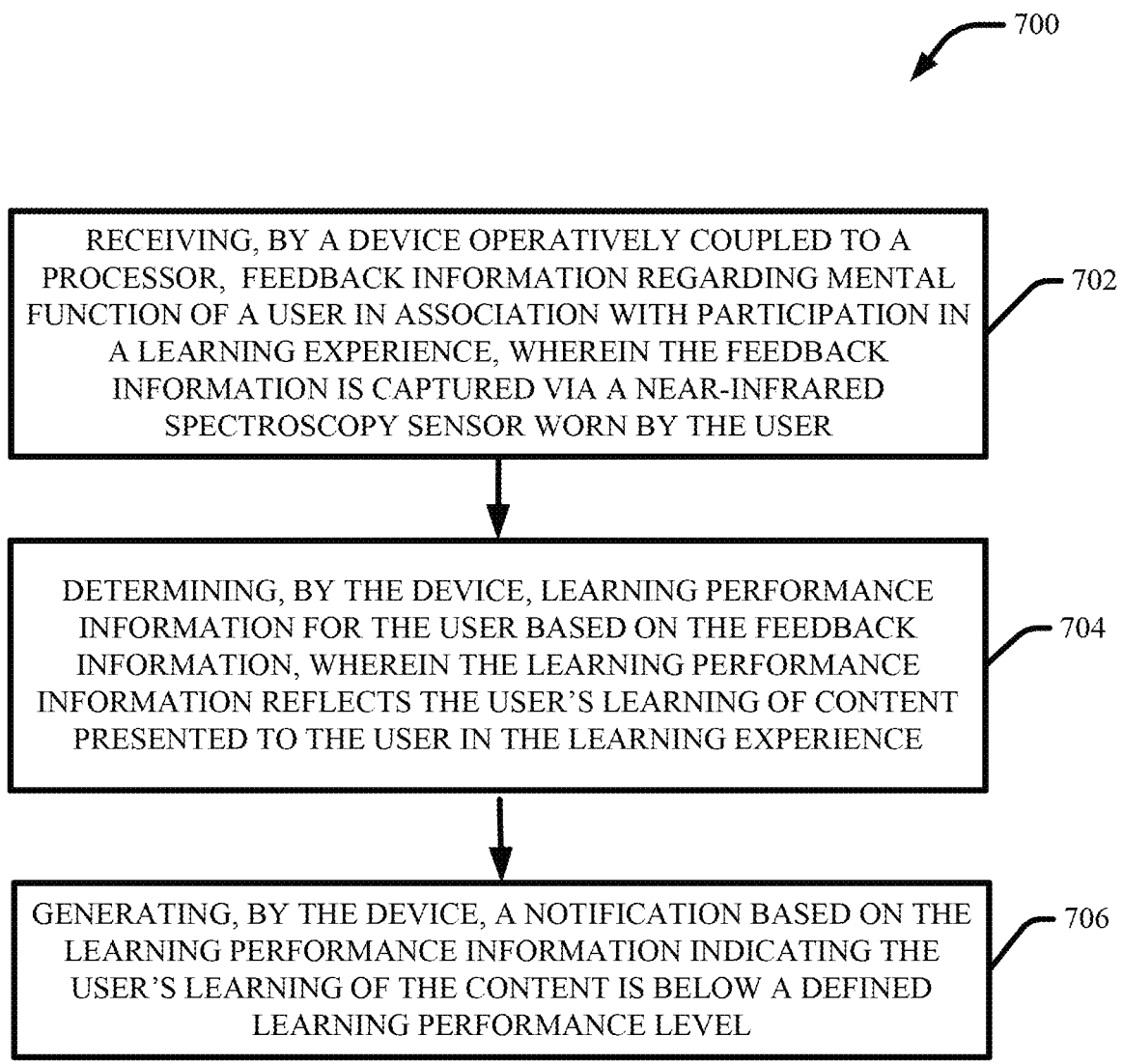
FIG. 7 illustrates a flow diagram of an example, non-limiting computer-implemented method that facilitates monitoring learning performance using neurofeedback in accordance with one or more embodiments described herein.

FIG. 7 illustrates a flow diagram of an example, non-limiting computer-implemented method 700 that facilitates that facilitates monitoring learning performance using neurofeedback in accordance with one or more embodiments described herein. Repetitive description of like elements employed in other embodiments described herein is omitted for sake of brevity.

At 702, a device operatively coupled to a processor (e.g., learning performance server device 106 or a student device 202) can receive feedback information (e.g., via feedback component 302) regarding mental function of a user in association with participation in a learning experience, wherein the feedback information is captured via a NIRS sensor worn by the user (e.g., one or more NIRS sensors 316). For example, the feedback information can include haemodynamic and metabolic information captured from the user via a neurofeedback device (e.g., neurofeedback device 102) worn by the user while the user engages in a live or recorded lecture, exam, group learning experience, self-study period, etc.). The haemodynamic information can indicate quantitative or qualitative measures of mental functioning of the user with respect to one or more defined cognitive function areas (e.g., working memory performance levels, stress/mental workload levels, and/or attention levels of the user).

At 704, the device can determine learning performance information for the user regarding the user based on the feedback information, wherein the learning performance information reflects the user's learning of content presented to the user in the learning experience (e.g., via assessment component 304). For example, the device can analyze the feedback information to identify patterns associated with concentrations of oxygenated-Hb levels in different areas or regions of the brain to determine values or scores representative of working memory performance levels, mental stress levels, and/or attention levels of the user over the course of the learning experience, wherein the respective values or scores, (or combinations of the respective values of scores), reflect different degrees of learning performance quality levels exhibited by the user (e.g., from an extremely good or high quality learning performance level to an extremely poor or low quality learning performance level). At 706, the device can further generate a notification based on the learning performance information indicating the user's learning of the content is below a defined learning performance level (e.g., via notification component 306). For example, the device can determine that the learning performance information indicates that the learning performance level of the user in one or more cognitive function areas is below a threshold or optimal learning performance level.

Figure 8:
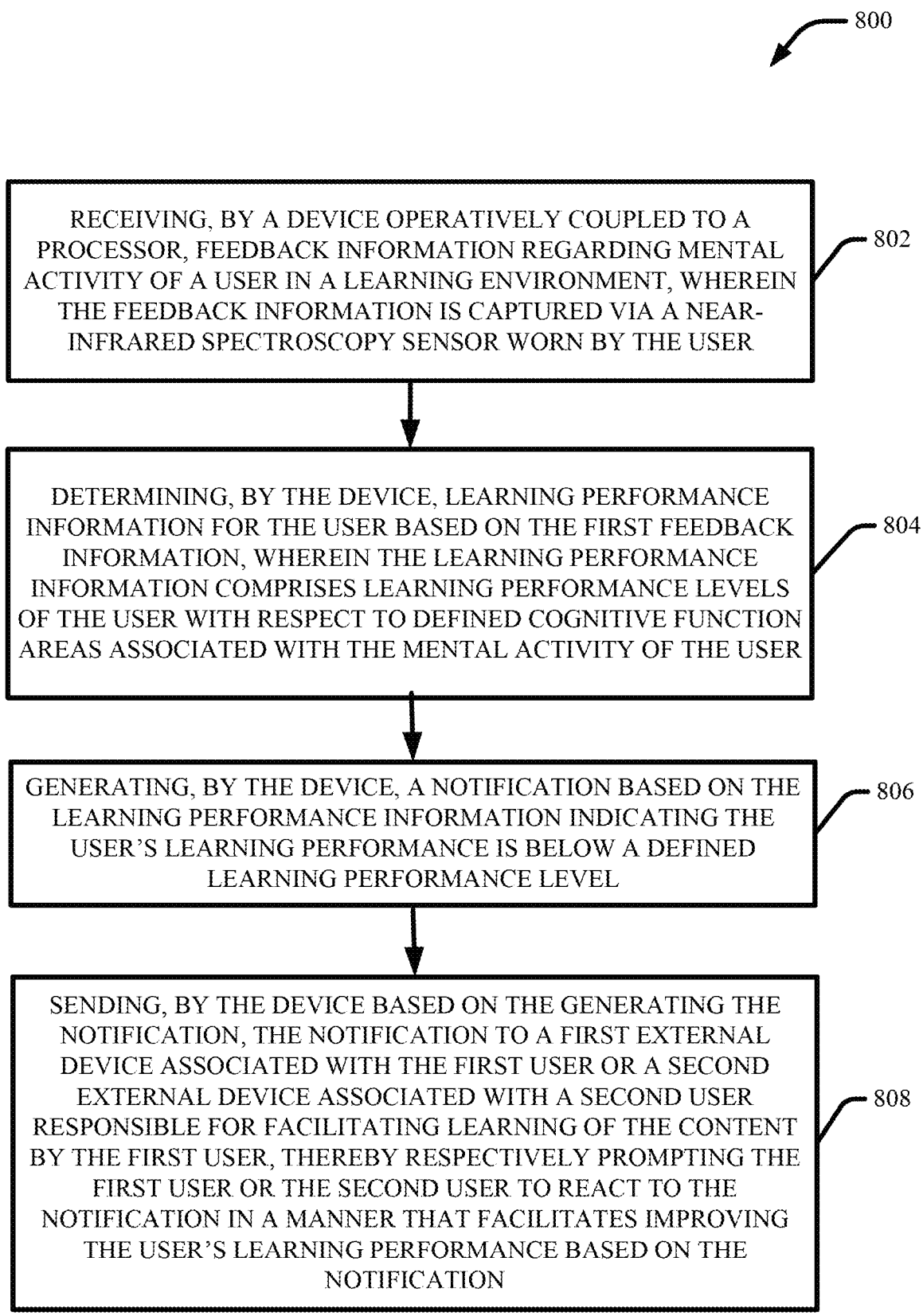
FIG. 8 illustrates a flow diagram of another example, non-limiting computer-implemented method that facilitates monitoring learning performance using neurofeedback in accordance with one or more embodiments described herein.

FIG. 8 illustrates a flow diagram of another example, non-limiting computer-implemented method 800 that facilitates that facilitates monitoring learning performance using neurofeedback in accordance with one or more embodiments described herein. Repetitive description of like elements employed in other embodiments described herein is omitted for sake of brevity.

At 802, a device operatively coupled to a processor (e.g., learning performance server device 106 or a student device 202) can receive feedback information (e.g., via feedback component 302) regarding mental activity of a user in a learning environment, wherein the feedback information is captured via a NIRS sensor worn by the user (e.g., one or more NIRS sensors 316). For example, the feedback information can include haemodynamic and metabolic information captured from the user via a neurofeedback device (e.g., neurofeedback device 102) worn by the user while the user engages in a live or recorded lecture, exam, group learning experience, self-study period, etc.). At 804, the device determines learning performance information for the user based on the first feedback information (e.g., using assessment component 304), wherein the learning performance information comprises learning performance levels of the user with respect to defined cognitive function areas associated with the mental activity of the user including determining performance levels of the user with respect to defined cognitive function areas associated with the mental activity of the user (e.g., working memory performance levels, stress/mental workload levels, and/or attention levels of the user).

At 806, the device generates a notification based on the learning performance information indicating the user's learning performance is below a defined learning performance level (e.g., via notification component 306). For example, the device can determine that the learning performance information indicates that the learning performance level of the user in one or more cognitive function areas is below a threshold or optimal learning performance level. At 808, the device sends, based on the generating the notification, the notification to a first external device associated with the first user (e.g., one of the student devices 202) or a second external device associated with a second user responsible for facilitating learning of the content by the first user (e.g., the teacher device 108), thereby respectively prompting the first user or the second user to react to the notification in a manner that facilitates improving the user's learning performance based on the notification.

Figure 9:
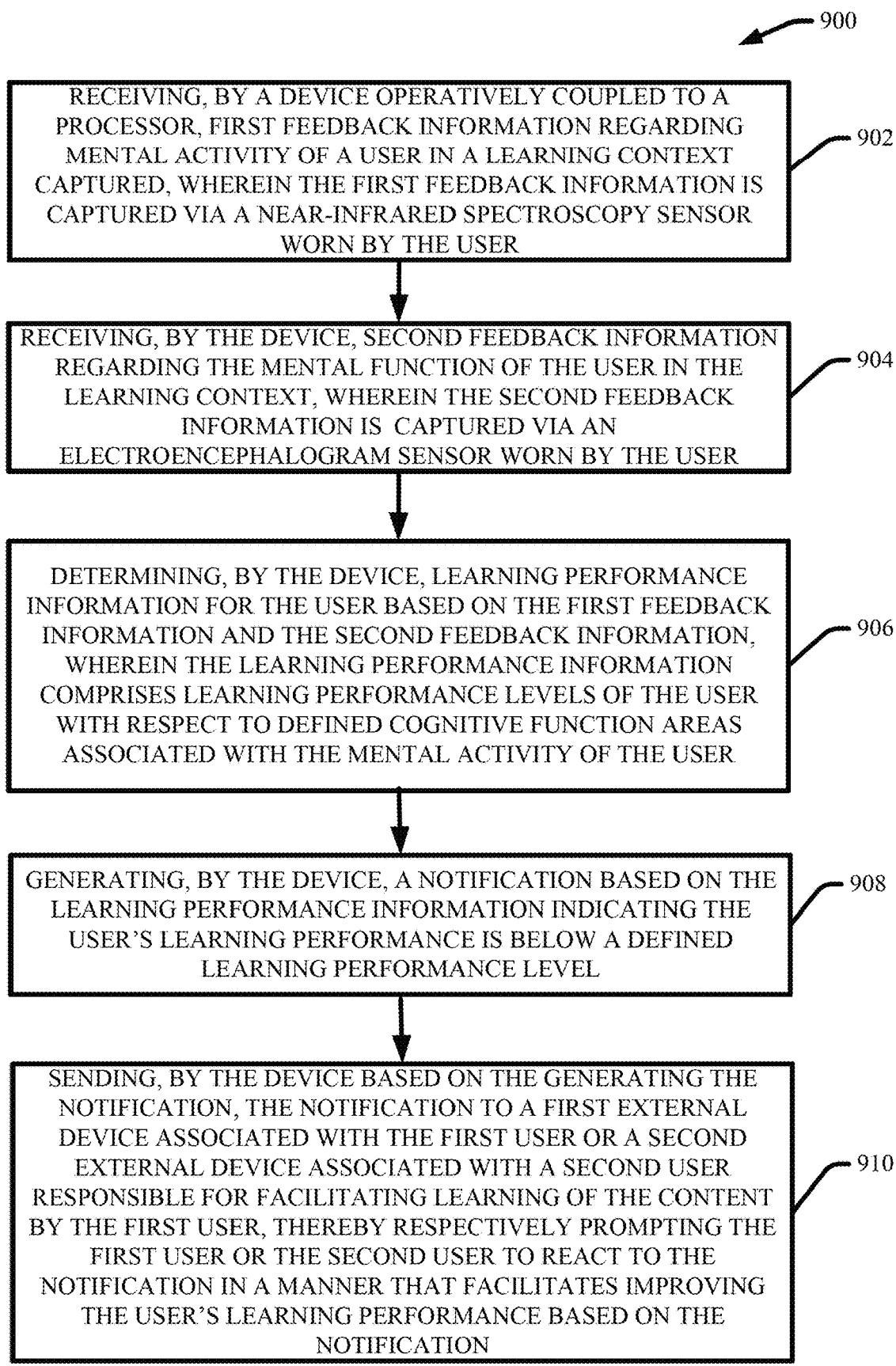
FIG. 9 illustrates a flow diagram of another example, non-limiting computer-implemented method that facilitates monitoring learning performance using neurofeedback in accordance with one or more embodiments described herein.

FIG. 9 illustrates a flow diagram of another example, non-limiting computer-implemented method 900 that facilitates that facilitates monitoring learning performance using neurofeedback in accordance with one or more embodiments described herein. Repetitive description of like elements employed in other embodiments described herein is omitted for sake of brevity.

At 902, a device operatively coupled to a processor (e.g., learning performance server device 106 or a student device 202) can receive first feedback information regarding mental activity of a user in a learning context captured, wherein the first feedback information is captured via a NIRS sensor worn by the user (e.g., via feedback component 302). At 904, the device can receive second feedback information regarding the mental function of the user in the learning context, wherein the first feedback information is captured via an EEG sensor worn by the user. For example, the EEG information can include brain waves captured from different areas of the brain over the course the learning context. At 906, the device determines learning performance information for the user based on the first feedback information and the second feedback information, wherein the learning performance information comprises learning performance levels of the user with respect to defined cognitive function areas associated with the mental activity of the user (e.g., attention, familiarity, mental effort, working memory, linguistic acquisition, social learning, and mediation).

At 908, the device generates a notification based on the learning performance information indicating the user's learning performance is below a defined learning performance level (e.g., via notification component 306). For example, the device can determine that the learning performance information indicates that the learning performance level of the user in one or more cognitive function areas is below a threshold or optimal learning performance level. At 910, the device sends, based on the generating the notification, the notification to a first external device associated with the first user (e.g., one of the student devices 202) or a second external device associated with a second user responsible for facilitating learning of the content by the first user (e.g., the teacher device 108), thereby respectively prompting the first user or the second user to react to the notification in a manner that facilitates improving the user's learning performance based on the notification.

Figure 10:
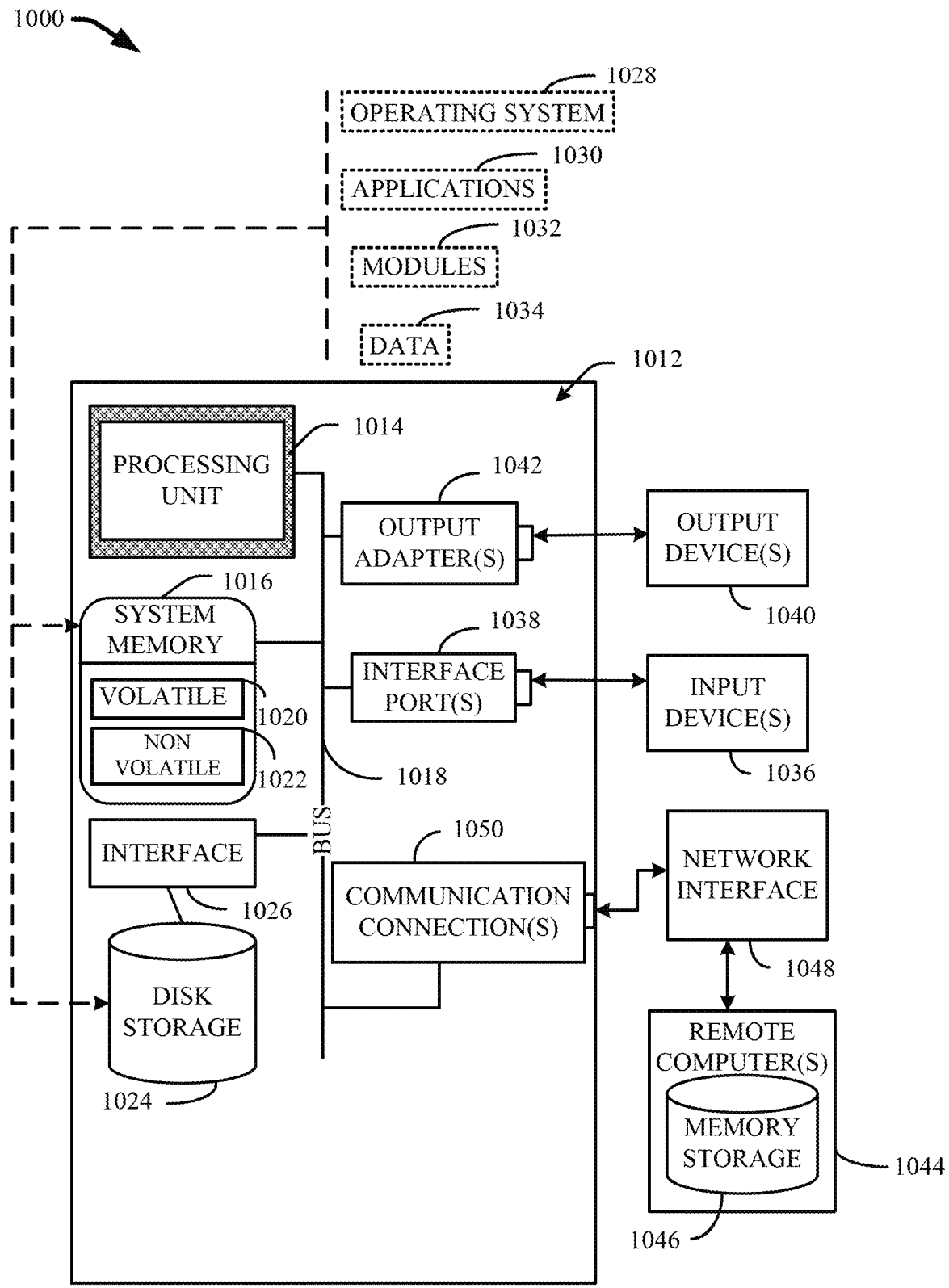
FIG. 10 illustrates a block diagram of an example non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity.

With reference to FIG. 10, a suitable operating environment 1001 for implementing various aspects of this disclosure can also include a computer 1012. In various embodiments, the neurofeedback device 102, the student device 202, the learning performance server device 106 and the teacher device 108 can be or include one or more components, features and functionalities of computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1094), and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/nonvolatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1001. Such software can also include, for example, an operating system 1028. Operating system 1028, which can be stored on disk storage 1024, acts to control and allocate resources of the computer 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a near-infrared spectroscopy sensor;
a memory that stores computer executable components; and
a processor that executes the computer executable components stored in the memory, wherein the computer executable components comprise:
 a feedback component that:
  captures, via the near-infrared spectroscopy sensor worn by a user, neuroimaging measurements including changes in blood oxygenation levels in different areas of a brain of the user during participation in a learning experience being presented by a teacher; and
  transforms the neuroimaging measurements into first feedback information representing brain activity over time in the different areas of the brain of the user;
 an assessment component that:
  identifies, via a pattern classifier, patterns of changes in brain activity in the first feedback information;
  determines learning performance information for the user based on correlating the patterns of changes in brain activity in the first feedback information to one or more performance measures associated with one or more defined cognitive function areas associated with the brain activity of the user, wherein the learning performance information reflects user learning of content presented to the user in the learning experience;
 a notification component that generates a notification on a first device associated with the teacher based on the learning performance information indicating the user learning of the content is below a defined learning performance threshold; and
 an aggregate component that employs a support vector machine to infer an action to be performed by the user based on the learning experience.

2. The system of claim 1, wherein the notification component further sends another notification to a second device associated with the user or a third device associated with another user responsible for facilitating learning of the content by the user.

3. The system of claim 1, wherein the notification identifies one or more areas of the presentation for which the user learning is below the defined learning performance level.

4. The system of claim 1, wherein the learning performance information comprises respective learning performance levels of the user for the one or more performance measures with respect to the one or more defined cognitive function areas associated with the brain activity of the user.

5. The system of claim 4, wherein the one or more defined cognitive function areas are selected from a group consisting of: working memory, mental effort, and attention.

6. The system of claim 4, wherein a content correlation component can determine a part of the content included in a presentation that is associated with reception of the first feedback information based on timing of reception of the first feedback information and a current time point or time frame associated with the presentation, thereby facilitating improved processing time for determining if the user is having difficulty learning the content and for notifying a second user regarding the user's difficulty.

7. The system of claim 1, wherein the first feedback information comprises haemodynamic information representative of a brain activity area selected from a group consisting of: working memory performance levels, stress levels, and attention levels of the user.

8. The system of claim 1, wherein the first feedback information comprises metabolic information representative of a brain activity area selected from a group consisting of: working memory performance levels, stress levels, and attention levels of the user.

9. The system of claim 1, wherein the feedback component further receives second feedback information regarding the brain activity of the user in association with the participation in the learning experience, wherein the second feedback information is captured via an electroencephalogram sensor worn by the user, and wherein the assessment component further determines the learning performance information for the user based on the first feedback information and the second feedback information, wherein the learning performance information comprises respective learning performance levels of the user with respect to the one or more defined cognitive function areas associated with the brain activity of the user.

10. The system of claim 9, wherein the one or more defined cognitive function areas are selected from a group consisting of: attention, familiarity, mental effort, working memory, linguistic acquisition, social learning, and mediation, wherein an aggregation component can analyze aggregated learning performance data to predict one or more learning experiences that can be used to improve a student learning experience.

11. The system of claim 1, wherein the computer-executable components further comprise:
 a review component that stores the learning performance information and facilitates review of the learning performance information by the user or another user responsible for facilitating learning of the content by the first user.

12. A computer implemented method, comprising:
 capturing, by a device operatively coupled to a processor, via a near-infrared spectroscopy sensor worn by a user, neuroimaging measurements including changes in blood oxygenation levels in different areas of a brain of the user during participation in a learning experience being presented by a teacher;
 transforming, by the device, the neuroimaging measurements into first feedback information representing brain activity over time in the different areas of the brain of the user;
 identifying, by the device via a pattern classifier, patterns of changes in brain activity in the first feedback information;
 determining, by the device, learning performance information for the user based on correlating the patterns of changes in brain activity in the first feedback information to one or more performance measures associated with one or more defined cognitive function areas associated with the brain activity of the user, wherein the learning performance information comprises respective learning performance levels of the user for the one or more performance measures with respect to the one or more defined cognitive function areas associated with the brain activity of the user;
 generating, by the device, a notification on a first device associated with the teacher based on the learning performance information indicating user learning performance is below a defined learning performance threshold; and
 employing, by the device, a support vector machine to infer an action to be performed by the user based on the learning experience.

13. The computer implemented method of claim 12, further comprising:
 sending, by the device based on the generating the notification, another notification to a second device associated with the user or a third device associated with another user responsible for facilitating learning of the content by the user.

14. The computer implemented method of claim 12, further comprising:
 obtaining by the device, video of the user during the presentation;
 analyzing, by the device, the video to obtain additional information selected from the group consisting of facial expressions of the user and body languages of the user;
 correlating, by the device, the additional information with the first feedback information to determine the learning performance information.

15. The computer implemented method of claim 12, further comprising:
 determining, by the device, a part of the content included in a presentation that is associated with reception of the first feedback information based on timing of reception of the first feedback information and a current time point or time frame associated with the presentation, and wherein the notification identifies the user, the one or more defined cognitive function areas, and the learning performance levels for the one or more defined cognitive function areas.

16. The computer implemented method of claim 12, wherein the first feedback information comprises haemodynamic information representative of a brain function area selected from a group consisting of: working memory performance levels, stress levels, and attention levels of the user.

17. The computer implemented method of claim 12, further comprising:
 receiving, by the device, second feedback information regarding the brain activity of the user in the learning environment, wherein the second feedback information is captured via an electroencephalogram sensor worn by the user, and wherein the determining the learning performance information comprises determining the learning performance information for the user based on the first feedback information and the second feedback information.

18. The computer implemented method of claim 12, wherein the one or more defined cognitive function areas are selected from a group consisting of: attention, familiarity, mental effort, working memory, linguistic acquisition, social learning, and mediation.

19. A computer program product for monitoring learning performance based on neurofeedback, the computer program product comprising a computer readable storage medium having program instructions embodied therewith, the program instructions executable by a processing component to cause the processing component to:
    capture, via a near-infrared spectroscopy sensor worn by a user, neuroimaging measurements including changes in blood oxygenation levels in different areas of a brain of the user during participation in a learning experience being presented by a teacher;
    transform the neuroimaging measurements into neurofeedback information representing brain activity over time in the different areas of the brain of the user based on the neuroimaging measurements;
    identifying, by the device via a pattern classifier, patterns of changes in brain activity in the neurofeedback information;
    determine learning performance information for the user based on correlating the patterns of changes in brain activity in the neurofeedback information to one or more performance measures associated with one or more defined cognitive function areas associated with the brain activity of the user, wherein the learning performance information reflects user learning of content presented to the user in the learning context by a teacher;
    generate a notification based on the learning performance information indicating the user learning of the content is below a defined learning performance threshold;
        send the notification to a device associated with the teacher to facilitate improving the user's learning of the content; and
    employ a support vector machine to infer an action to be performed by the user based on the learning experience.

20. The computer program product of claim 19, wherein the learning performance information comprises respective learning performance levels of the user for the one or more performance measures with respect to the one or more defined cognitive function areas associated with the brain activity of the user, wherein the one or more defined cognitive function areas comprise one or more of: attention, familiarity, mental effort, working memory, linguistic acquisition, social learning, and mediation, wherein analyze aggregated learning performance information to predict one or more learning experiences that can be used to improve a student learning experience.

* * * * *